(12) United States Patent
Leeds et al.

US008506957B2

(10) Patent No.: US 8,506,957 B2
(45) Date of Patent: Aug. 13, 2013

(54) METHODS AND COMPOSITIONS FOR MONITORING PROGRESSION OF HUNTINGTON'S DISEASE

(75) Inventors: Nicola Louise Leeds, Tonbridge (GB); Malcolm Andrew Ward, Shefford (GB); Sarah Joanna Tabrizi, London (GB); Annette Dalrymple, London (GB); Emma McGregor, London (GB); James Campbell, London (GB); Jules Arthur Westbrook, Middlesex (GB); Helen Louise Byers, London (GB)

(73) Assignee: Electrophoretics Limited, Cobham, Surrey (GB)

( * ) Notice: Subject to any disclaimer, the term of this patent is extended or adjusted under 35 U.S.C. 154(b) by 860 days.

(21) Appl. No.: 11/792,758

(22) PCT Filed: Dec. 7, 2005

(86) PCT No.: PCT/GB2005/004700
§ 371 (c)(1),
(2), (4) Date: May 16, 2008

(87) PCT Pub. No.: WO2006/061610
PCT Pub. Date: Jun. 15, 2006

(65) Prior Publication Data
US 2008/0286263 A1    Nov. 20, 2008

(30) Foreign Application Priority Data

Dec. 7, 2004  (GB) .................... 0426859.5
Oct. 25, 2005  (GB) .................... 0521762.5

(51) Int. Cl.
*A61K 39/395* (2006.01)
*G01N 33/68* (2006.01)
(52) U.S. Cl.
USPC ..................... 424/130.1; 435/7.92

(58) Field of Classification Search
None
See application file for complete search history.

(56) References Cited

U.S. PATENT DOCUMENTS

2006/0094039 A1* 5/2006 Rosenfeld et al. ............... 435/6
2008/0070995 A1* 3/2008 Westbrook et al. ............ 514/789
2008/0213801 A1* 9/2008 Wu et al. ....................... 435/7.5

OTHER PUBLICATIONS

Morrissey C et al. An antigen capture assay for the measurement of serum clusterin concentrations. J. Biochem. Biophys. Methods, 2001; 48:13-21.*

(Continued)

*Primary Examiner* — Jeffrey Stucker
*Assistant Examiner* — Adam M Weidner
(74) *Attorney, Agent, or Firm* — Arent Fox LLP

(57) ABSTRACT

The invention relates to a method of diagnosis of Huntington's Disease in a diagnostic sample of a valid body tissue taken from a human subject, which comprises detecting an altered concentration of a protein in the diagnostic sample, compared with a sample of a control human subject, the protein being selected from: Swiss Prot accession number: Protein name; P10909: Clusterin precursor; P00738: Haptoglobin precursor; P01009: Alpha-1-antitrypsin precursor; P01024: Complement C3 precursor; P01620: 1g kappa chain V-III region; P01834: 1 g kappa chain C region P01842: 1g lambda chain C regions; P01857: 1g gamma-1 chain C region; P01859: Ig gamma-2 chain C region; P01876: 1g alpha-1 chain C region P02647: Apolipoprotein A-I precursor; P02649: Apolipoprotein E precursor; P02652: Apolipoprotein A-II precursor; P02655: Apolipoprotein C-II precursor; P02656: Apolipoprotein C-II precursor P02671: Fibrinogen alpha/alpha-E chain precursor; P02763: Alpha-1-acid glycoprotein 1 precursor; P02766: Transthyretin precursor; P02768: Serum albumin precursor; P02787: Serotransferrin precursor; P04196: Histidine-rich glycoprotein precursor; P06727: Apolipoprotein A-IV precursor; P19652: Alpha-1-acid glycoprotein 2 precursor; P68871/P02042: Hemoglobin beta chain/Hemoglobin delta chain; P60709: Beta actin.

16 Claims, 17 Drawing Sheets

(56) References Cited

OTHER PUBLICATIONS

Nilselid AM et al. Clusterin in cerebrospinal fluid: Analysis of carbohydrates and quantification of native and glycosylated forms. Neurochem. Int. 2006; 48:718-728.*

Wong et al. 1994 "Molecular characterization of human TRPM-2/clusterin, a gene associated with sperm maturation, apoptosis and neurodegeneration" Eur J Biochem 221:917-925.*

P.L. McGeer et al., Distribution of clusterin in Alzheimer brain tissue; *Elsevier Science publishers B.V.*, Jan. 1992.

Wellmann, A., Detection of differentially expressed genes in lymphomas using cDNA arrays: identification of clusterin as a new diagnostic marker for anaplastic large-cell lymophomas; Blood, 2000; 96(2):398-404.

M. Freixes et al., Clusterin solubility and aggregation in Creutzfeldt-Jakob disease; *Acta neuropathology* (2004) 108: 295-301.

J. Dieter et al.; Clusterin (Complement Lysis Inhibitor) Forms a High Density lipoprotein Complex with Apolipoprotein A-I in Human Plasma; *The Journal of Biological Chemistry*; 1991; vol. 266, No. 17, pp. 11030-11036.

Albert, S. et al., Towards a high resolution separation of human cerebrospinal fluid; *Journal of Chromatography*, 771 (2002) pp. 167-196.

S.K. Singhrao et al., Increase Complement Biosynthesis by Microglia and Complement Activation on Neurons in Huntington's Disease; *Experimental Neurology* 1999, 159, pp. 362-376.

International Search Report PCT/GB2005/004700 filed Dec. 7, 2005.

WO 2004/007675 A Intl. Publication Date Jan. 22, 2004; Intl. Application No. PCT/US2003/021738.

\* cited by examiner

M > C, p = 0.003
M > P, p = 0.002

METHODS AND COMPOSITIONS FOR MONITORING PROGRESSION OF HUNTINGTON'S DISEASE

RELATED APPLICATION INFORMATION

This application is a 371 national stage entry of PCT/GB2005/004700, filed Dec. 7, 2005, which claims the benefit of priority from UK application no. 0521762.5, filed on Oct. 25, 2005, and UK application no. 0426859.9, filed on Dec. 7, 2004.

BACKGROUND OF THE INVENTION

1. Field of the Invention

This invention relates to the diagnosis of neurodegenerative diseases, namely Huntington's Disease (HD).

2. Description of the Related Art

Huntington's disease is autosomal dominantly inherited and is caused by a CAG repeat expansion in the IT15 gene on chromosome 4, resulting in production of a long polyglutamine stretch. The disease is associated with progressive and severe degeneration of the striatum and cortex of the brain, and is clinically characterised by a movement disorder, behavioural problems and dementia. The mean age of onset is 40 years and life expectancy is 15-20 years.

The disease is clinically heterogeneous and there are difficulties in the assessment of disease progression in this illness that have led to the need for further methods to be developed to aid the development of therapeutic trials for this disease.

SUMMARY OF THE INVENTION

The invention provides the use of specified marker proteins and their partners in or for the diagnosis of HD. These marker proteins have been found to be differentially expressed in two dimensional electrophoresis of plasma samples and Surface Enhanced Laser Desorption Ionisation (SELDI) time of flight mass spectrometry profiling experiments.

The marker proteins and their differential expression characteristics are as follows:

1. Protein present in an increased concentration in a HD sample, compared with a control: clusterin precursor (SwissProt Acc. No. P10909);
2. Further proteins present in an increased or decreased concentration in a HD sample, compared with a control, as listed below;
3. Proteins present in an increased concentration in HD samples, compared with a control: beta-actin (SwissProt Acc. No. P60709) and apolipoprotein A-IV precursor (SwissProt Acc. No. P06727).

Thus, the invention includes specifically:

1. A method of diagnosis of Huntington's Disease, including assessment of disease stage, in a diagnostic sample of a valid body tissue taken from a human subject, which comprises detecting an altered concentration of a protein in the diagnostic sample, compared with a sample of a control human subject, the protein being selected from:

| Swiss Prot accession number | Protein name |
|---|---|
| P10909 | Clusterin precursor |
| P00738 | Haptoglobin precursor |
| P01009 | Alpha-1-antitrypsin precursor |
| P01024 | Complement C3 precursor |
| P01620 | Ig kappa chain V-III region |
| P01834 | Ig kappa chain C region |
| P01842 | Ig lambda chain C regions |
| P01857 | Ig gamma-1 chain C region |
| P01859 | Ig gamma-2 chain C region |
| P01876 | Ig alpha-1 chain C region |
| P02647 | Apolipoprotein A-I precursor |
| P02649 | Apolipoprotein E precursor |
| P02652 | Apolipoprotein A-II precursor |
| P02655 | Apolipoprotein C-II precursor |
| P02656 | Apolipoprotein C-III precursor |
| P02671 | Fibrinogen alpha/alpha-E chain precursor |
| P02763 | Alpha-1-acid glycoprotein 1 precursor |
| P02766 | Transthyretin precursor |
| P02768 | Serum albumin precursor |
| P02787 | Serotransferrin precursor |
| P04196 | Histidine-rich glycoprotein precursor |
| P06727 | Apolipoprotein A-IV precursor |
| P19652 | Alpha-1-acid glycoprotein 2 precursor |
| P68871/P02042 | Hemoglobin beta chain/Hemoglobin delta chain |
| P60709 | Beta actin |

2. A method as defined in 1 above, which comprises detecting an increased concentration of a protein in the diagnostic sample, compared with a sample of a control human subject, the protein being a clusterin precursor (SwissProt Acc No. P10909).

3. A method according to claim 1, which comprises detecting an increased concentration of a protein in the diagnostic sample, compared with a sample of a control human subject, the protein being:

beta actin (SwissProt Acc. No. P60709) or
apolipoprotein A-IV precursor (SwissProt Acc. No. P06727).

The marker protein can be present in the body tissue in any biologically relevant form, e.g. in a glycosylated, phosphorylated, multimeric or precursor form.

Although there is a high degree of confidence in the identification of the marker proteins specified above, the invention can be defined alternatively in terms of the proteins within the differentially expressed spots on a two dimensional electrophoretic gel, namely those identified in FIG. 2 herein, without regard to the names and database identifications given above.

DEFINITIONS

The term "differentially expressed" means that the stained protein-bearing spots are present at a higher or lower optical density in the gel from the sample taken for diagnosis (the "diagnostic sample") than the gel from a control or other comparative sample. It follows that the proteins are present in the plasma of the diagnostic sample at a higher or lower concentration than in the control or other comparative sample.

The term "control" refers to a normal human subject, i.e. one not suffering from a neurodegenerative disease, and also to a sample taken from the same human subject that provided the diagnostic sample, but at an earlier time.

The terminology "increased/decreased concentration . . . compared with a sample of a control" does not imply that a step of comparing is actually undertaken, since in many cases it will be obvious to the skilled practitioner that the concentration is abnormally high. Further, when the stages of HD are being monitored progressively, the comparison made can be with the concentration previously seen in the same subject in earlier progression of the disease.

The term "binding partner" includes a substance that recognises or has affinity for the marker protein. It may or may not itself be labelled.

The term "marker protein" includes all biologically relevant forms of the protein identified.

The term "diagnosis", as used herein, includes determining whether the relevant disease is present or absent and also includes, in relation to Huntington's Disease, determining the stage to which it has progressed. The diagnosis can serve as the basis of a prognosis as to the future outcome for the patient and for monitoring efficacy of treatment.

The term "valid body tissue" means any tissue in which it may reasonably be expected that a marker protein would accumulate in relation to HD. While it will principally be a body fluid, it also includes brain or nerve tissue, it being understood that the diagnosis can be post mortem.

DESCRIPTION OF PREFERRED EMBODIMENTS

Figure 1:
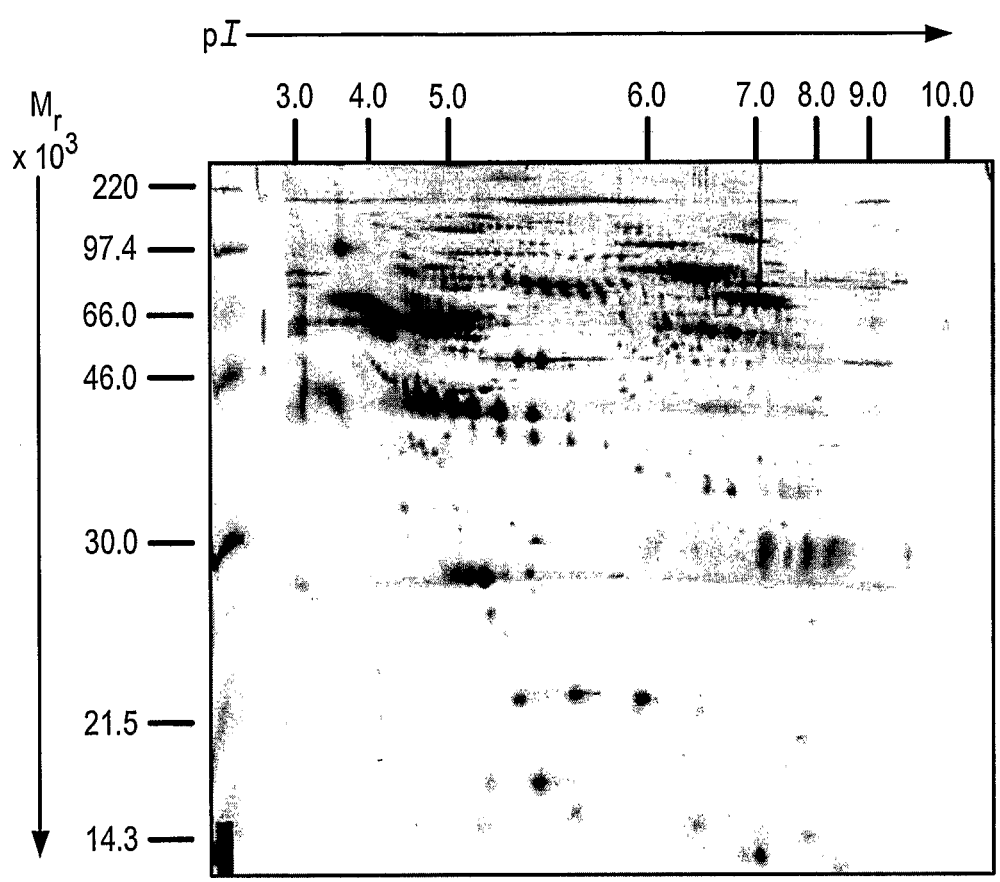
FIG. 1 is a photograph of a typical two dimensional gel performed for analytical purposes, by the method described in Example 1 below. The molecular weight (relative molecular mass) is shown on the ordinate in kiloDaltons. Molecular weight markers are shown at the left-hand side. The isoelectric point (pI) is shown on the ordinate, increasing from left to right.

A preferred method of diagnosis comprises performing a binding assay for the marker protein. Any reasonably specific binding partner can be used. Preferably the binding partner is labelled. Preferably the assay is an immunoassay, especially between the marker and an antibody that recognises the protein, especially a labelled antibody. It can be an antibody raised against part or all of it, most preferably a monoclonal antibody or a polyclonal anti-human antiserum of high specificity for the marker protein.

Thus, the marker proteins described above are useful for the purpose of raising antibodies thereto which can be used to detect the increased or decreased concentration of the marker proteins present in a diagnostic sample. Such antibodies can be raised by any of the methods well known in the immunodiagnostics field.

The antibodies may be anti- to any biologically relevant state of the protein. Thus, for example, they could be raised against the unglycosylated form of a protein which exists in the body in a glycosylated form, against a more mature form of a precursor protein, e.g. minus its signal sequence, or against a peptide carrying a relevant epitope of the marker protein.

The sample can be taken from any valid body tissue, especially body fluid, of a (human) subject, but preferably blood, plasma or serum. Other usable body fluids include cerebrospinal fluid (CSF), urine and tears.

According to another embodiment of the invention, the diagnosis is carried out post mortem on a body tissue of neurological origin relevant to HD, such as from the brain or nerves. The tissue is pre-treated to extract proteins therefrom, including those that would be present in the blood of the deceased, so as to ensure that the relevant marker proteins specified above will be present in a positive sample. For the purposes of this patent specification, such an extract is equivalent to a body fluid.

By way of example, brain tissue is dissected and subsections solubilised in 2-D gel lysis buffer (e.g. as described below), in a ratio of about 100 mg tissue to 1 ml buffer.

The preferred immunoassay is carried out by measuring the extent of the protein/antibody interaction. Any known method of immunoassay may be used. A sandwich assay is preferred. In this method, a first antibody to the marker protein is bound to the solid phase such as a well of a plastics microtitre plate, and incubated with the sample and with a labelled second antibody specific to the protein to be assayed. Alternatively, an antibody capture assay could be used. Here, the test sample is allowed to bind to a solid phase, and the anti-marker protein antibody is then added and allowed to bind. After washing away unbound material, the amount of antibody bound to the solid phase is determined using a labelled second antibody, anti- to the first.

In another embodiment, a competition assay is performed between the sample and a labelled marker protein or a peptide derived therefrom, these two antigens being in competition for a limited amount of anti-marker protein antibody bound to a solid support. The labelled marker protein or peptide thereof could be pre-incubated with the antibody on the solid phase, whereby the marker protein in the sample displaces part of the marker protein or peptide thereof bound to the antibody.

In yet another embodiment, the two antigens are allowed to compete in a single co-incubation with the antibody. After removal of unbound antigen from the support by washing, the amount of label attached to the support is determined and the amount of protein in the sample is measured by reference to standard titration curves established previously.

The label is preferably an enzyme. The substrate for the enzyme may be, for example, colour-forming, fluorescent or chemiluminescent.

The binding partner in the binding assay is preferably a labelled specific binding partner, but not necessarily an antibody. For example, when the marker protein is alpha-1-antitrypsin, the specific binding partner can be trypsin. The binding partner will usually be labelled itself, but alternatively it may be detected by a secondary reaction in which a signal is generated, e.g. from another labelled substance.

It is highly preferable to use an amplified form of assay, whereby an enhanced "signal" is produced from a relatively low level of protein to be detected. One particular form of amplified immunoassay is enhanced chemiluminescent assay. Conveniently, the antibody is labelled with horseradish peroxidase, which participates in a chemiluminescent reaction with luminol, a peroxide substrate and a compound which enhances the intensity and duration of the emitted light, typically 4-iodophenol or 4-hydroxycinnamic acid.

Another preferred form of amplified immunoassay is immuno-PCR. In this technique, the antibody is covalently linked to a molecule of arbitrary DNA comprising PCR primers, whereby the DNA with the antibody attached to it is amplified by the polymerase chain reaction. See E. R. Hendrickson et al., Nucleic Acids Research 23: 522-529 (1995). The signal is read out as before.

Alternatively, the diagnostic sample can be subjected to two dimensional gel electrophoresis to yield a stained gel and the increased or decreased concentration of the protein detected by an increased an increased or decreased intensity of a protein-containing spot on the stained gel, compared with a corresponding control or comparative gel. The relevant spots, diseases identified and differential expression are those listed in Table 1 below. The invention includes such a method, independently of the marker protein identification given above and in Table 2.

The diagnosis does not necessarily require a step of comparison of the concentration of the protein with a control, but it can be carried out with reference either to a control or a comparative sample. Thus, in relation to Huntington's disease the invention can be used to determine the stage of progression, if desired with reference to results obtained earlier from the same patient or by reference to standard values that are considered typical of the stage of the disease. In this way, the invention can be used to determine whether, for example after treatment of the patient with a drug or candidate drug, the disease has progressed or not. The result can lead to a prognosis of the outcome of the disease.

Figure 2:
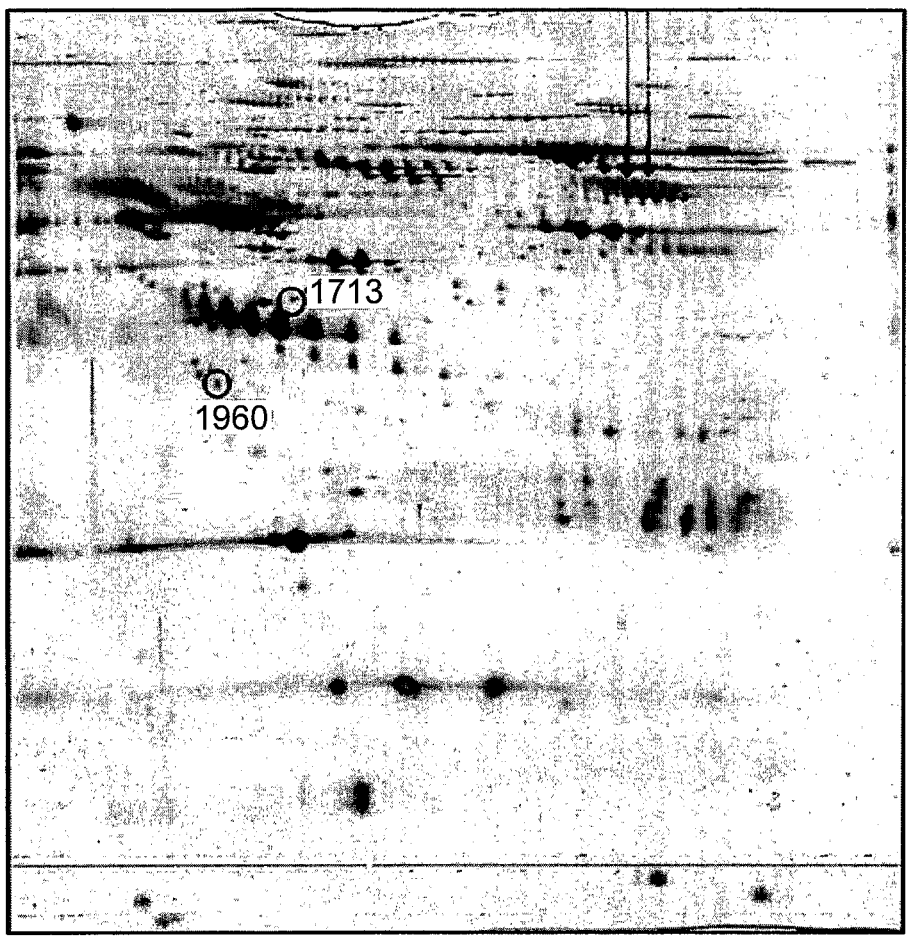
FIG. 2 is similar to FIG. 1, but showing spots 1713 and 1960 in a sample derived from an HD patient.

The invention further includes the use for a diagnostic (and thus possibly prognostic) or therapeutic purpose of a partner material which recognises, binds to or has affinity for a marker protein specified above and/or represented by a differentially expressed two dimensional gel electrophoretic spot shown in FIG. 2 herein. Thus, for example, antibodies to the marker proteins, appropriately humanised where necessary, may be used to treat HD. The partner material will usually be an antibody and used in any assay-compatible format, conveniently an immobilised format, e.g. as beads or a chip. Either the partner material will be labelled or it will be capable of interacting with a label.

The invention further includes a kit for use in a method of diagnosis, which comprises a partner material, as described above, in an assay-compatible format, as described above, for interaction with a protein present in the diagnostic sample.

The diagnosis can be based on the differential expression of one, two, three or more of the marker proteins. Further, it can be part of a wider diagnosis in which two or more different diseases are diagnosed. Both vCJD and Huntington's can be diagnosed together and either or both of those along with at least one other disease, which may or may not be neurological, in the same sample of body fluid, by a method which includes detecting an increased concentration of another protein in the diagnostic sample, compared with a sample of a control, normal human subject. These other disease(s) can be any which are diagnosable in a body fluid. They may be neurological, e.g. another transmissible spongiform encephalopathy, Parkinson's Disease, meningitis, but are not necessarily neurological, for example toxic shock syndrome, MRSA or Celiac disease.

Thus, in particular, it is contemplated within the invention to use an antibody chip or array of chips, capable of diagnosing one or more proteins that interact with that antibody.

The following Examples illustrate the invention.

EXAMPLE 1

Ten plasma samples were taken from patients (4 female, 6 male) who were diagnosed with variant CJD (vCJD) serving as a neurological disease control, ten from patients (7 female, 3 male) diagnosed by genetic testing as having Huntington's Disease (HD) and ten from controls, i.e. normal patients (8 female, 2 male) not having any neuropathological symptoms.

Albumin and IgG were removed from the samples using a kit supplied by Amersham Biosciences UK Ltd. This kit contains an affinity resin containing antibody that specifically removes albumin and IgG directly from whole human serum and plasma samples. It is claimed that more than 95% albumin and more than 90% IgG removal from 15 µl human serum/plasma can be achieved, thereby increasing the resolution of lower abundance proteins in subsequent electrophoresis. A microspin column is used, through which the unbound protein is eluted.

Depletion was carried out according to the manufacturer's instructions using a starting volume of 15 µl of crude plasma sample. The resin was added to the plasma, the mixture incubated with shaking, transferred to a microspin column, centrifuged and the filtrate collected. The resulting depleted sample was concentrated and de-salted by acetone precipitation (as recommended in the instructions of the kit). The acetone was decanted and the pellets were re-suspended in standard 2-D gel lysis buffer (9.5 M urea, 2% CHAPS, 1% DTT, 0.8% Pharmalyte, pH 3-10, protease inhibitors (1 tablet/10 ml lysis buffer) (Roche). This suspension was used for the two dimensional gel electrophoresis.

Since the depletion kit does not provide the user with a protocol to "strip off" the proteins bound to the column, a standard chromatography method was adopted for doing this, which is to use a 0.1 M Glycine-HCl, pH 2.5 buffer. All corresponding bound fractions were stored at –80° C. for later use in another experiment.

Two dimensional gel electrophoresis was performed according to J. Weekes et al., Electrophoresis 20: 898-906 (1999) and M. Y. Heinke et al., Electrophoresis 20: 2086-2093 (1999), using 18 cm immobilised pH 3-10 non-linear gradient strips (IPGs). The second dimension was performed using 12% T SDS polyacrylamide gel electrophoresis. For the initial analysis, the gels were loaded with 75 micrograms of protein. The gels were silver-stained with the analytical OWL silver stain (Insight Biotechnologies, UK).

Quantitative and qualitative image analysis was performed using the software Progenesis™ Workstation, version 2003.02 (Nonlinear Dynamics Ltd.). The images were processed through the automatic wizard for spot detection, warping and matching. Thereafter, all images underwent extensive manual editing and optimal matching to the reference gel (>80% per gel). Following background subtraction and normalisation to total spot volume, protein spot data was exported to Excel for quantitative statistical analysis and comparisons of qualitative changes.

The student t-test, at the 95% confidence interval, was performed for every protein spot that could be compared between the samples from the diseased patients and the controls and which was present in at least 60% of the gels of each group, i.e. at least 6. A log transformation was performed, since this gave a more normal distribution, thus better meeting the assumptions of this test as applied to independent samples.

The spots for which a significant increase or decrease was observed in comparisons between the three groups are shown in FIG. 2 and listed in Table 1.

TABLE 1

| Spot No. | FIG. | Quantitative change (Increase/Decrease in intensity of spot in comparisons between vCJD, HD and control samples). | p value (t-test) |
|---|---|---|---|
| 1713 | 2 | Inc. vCJD vs. Control | 0.003 |
| 1713 | 5 | Inc. HD vs. Control | 0.000065 |
| 1960 | 5 | Inc. HD vs. Control | 0.004 |

It will be seen that spot 1713 is one to which particularly high confidence in the results can be attached in relation to the increase in its intensity in the HD samples versus controls.

For preparative purposes, further two dimensional gels were then made by the same method, by pooling all samples within each experimental group and loading the gels with 400 micrograms of protein. There were thus three gels prepared, one for each group, which were silver stained, using PlusOne silver stain (Amersham Pharmacia Biosciences UK Ltd.).

Normally, the spots were excised from the preparative gels in which they were elevated in intensity, but where this was not possible, they were excised from another gel. After in-gel reduction, alkylation and digestion of the excised material with trypsin, the peptides produced were extracted and subsequently analysed by LC/MS/MS. This procedure involves separation of the peptides by reversed phase HPLC, followed by electrospraying to ionise the sample, as it enters a tandem mass spectrometer. The mass spectrometer records the mass to charge ratio of the peptide precursor ions, which are then individually selected for fragmentation via collisionally induced dissociation (CID). This so-called MS/MS scan allows for the sequence of the peptide to be determined. For each sample, therefore, the data set includes accurately determined molecular weights for multiple peptides present, accompanied by corresponding sequence information. This is then used to identify the protein by searching databases. In the present case, the Mascot search algorithm was used against the National Center for Biotechnology Information (NCBI) non-redundant protein (nr) and SWISS-PROT databases.

The results of the identification are shown in Table 2. All the spots of Table 1 that were differentially expressed on the gel were identified as known proteins. The Table shows the geninfo (gi) numbers of the NCBI database and SwissProt Accession numbers.

In some instances more than one protein was identified, which signifies that the spot excised contained a mixture of proteins, at least one of which was differentially expressed on the gel. The proteins identified in the database had different molecular weights and isoelectric points, lower or higher, from those evident on the gel. This is entirely usual and can be accounted for by the protein within the gel spot having undergone enzymatic or chemical cleavage or by having been post-translationally modified such as by glycosylation, phosphorylation or the addition of lipids.

TABLE 2

| Spot No. | MW (Da) from gel | pI from gel | Human protein identified | NCBI nr and SwissProt Acc. No. | No. peptides matched (% coverage) |
|---|---|---|---|---|---|
| 1713 | 43108 | 5.19 | Beta actin | gi/4501885 P60709 | 14 (47%) |
|  |  |  | Apolipoprotein A-IV precursor | gi/4502151 P06727 | 7 (26%) |
| 1960 | 33348 | 4.77 | Clusterin | gi/116533 P10909 | 8 (19%) |

EXAMPLE 2

The following Western blotting experiments were performed to show the use of the invention for monitoring the progression of Huntington's Disease.

Plasma samples were obtained, with appropriate consents, from 55 patients having various stages of Huntington's Disease and from 15 normal patients, as controls. The experimental groups were: control, pre-symptomatic (PST or P), early (E), moderate (M), 15 samples each and advanced (A), 10 samples. The samples were diluted 1 in 300 with sterile PBS (Sigma) and the protein concentration determined in triplicate, using BSA as a standard and the DC protein assay kit (Bio-Rad Laboratories Ltd, Herts, UK). Master mixes of plasma proteins were subsequently prepared to limit pipetting error and freeze-thawing and to enable identical samples to be run on a number of gels.

The samples were denatured at 95° C. for 10 min in Laemmli sample buffer (Sigma) and size-separated using 20 cm×10 cm 12% or 16% Tris-Glycine acrylamide gels (Gel tank: Sci-Plas, Southam, UK). Plasma samples were loaded in groups of 2-4 (see Table 3) to distribute samples over the gel and to limit differences in gel running and transfer efficiency. Proteins were transferred to polyvinylidene difluoride membranes (Amersham Pharmacia Biotech Ltd, Buckinghamshire, UK) for 30 min at 25 volts using a semi-dry blotting apparatus, Trans-Blot SD (Bio-Rad Laboratories Ltd).

TABLE 3

| | Gel 1 | | | Gel 2 | |
|---|---|---|---|---|---|
| Well | HD Disease Stage | Sample No | Well | HD Disease Stage | Sample No |
| 1 | | Markers | 1 | | Markers |
| 2 | Control | 1 | 2 | Control | 9 |
| 3 | Control | 2 | 3 | Control | 10 |
| 4 | Control | 3 | 4 | Control | 11 |
| 5 | PST | 16 | 5 | PST | 23 |
| 6 | PST | 17 | 6 | PST | 24 |
| 7 | PST | 18 | 7 | PST | 25 |
| 8 | Early | 31 | 8 | PST | 26 |
| 9 | Early | 32 | 9 | Early | 38 |
| 10 | Early | 33 | 10 | Early | 39 |
| 11 | Mod | 46 | 11 | Early | 40 |
| 12 | Mod | 47 | 12 | Early | 41 |
| 13 | Mod | 48 | 13 | Mod | 54 |
| 14 | Mod | 49 | 14 | Mod | 55 |
| 15 | ADV | 61 | 15 | Mod | 56 |
| 16 | ADV | 62 | 16 | Mod | 57 |
| 17 | ADV | 63 | 17 | ADV | 66 |
| 18 | Control | 4 | 18 | ADV | 67 |
| 19 | Control | 5 | 19 | ADV | 68 |
| 20 | PST | 19 | 20 | Control | 12 |
| 21 | PST | 20 | 21 | Control | 13 |
| 22 | PST | 21 | 22 | PST | 27 |
| 23 | PST | 22 | 23 | PST | 28 |
| 24 | Early | 34 | 24 | PST | 29 |
| 25 | Early | 35 | 25 | PST | 30 |
| 26 | Early | 36 | 26 | Early | 42 |
| 27 | Early | 37 | 27 | Early | 43 |
| 28 | Mod | 50 | 28 | Early | 44 |
| 29 | Mod | 51 | 29 | Early | 45 |
| 30 | Mod | 52 | 30 | Mod | 58 |
| 31 | Mod | 53 | 31 | Mod | 59 |
| 32 | ADV | 64 | 32 | Mod | 60 |
| 33 | ADV | 65 | 33 | ADV | 69 |
| 34 | Control | 6 | 34 | ADV | 70 |
| 35 | Control | 7 | 35 | Control | 14 |
| 36 | Control | 8 | 36 | Control | 15 |

The transfer efficiency and equal loading of protein samples was assessed by incubating membranes with Ponceau red solution (Sigma).

After transfer, membranes were washed with PBS-T (PBS, 0.1% Tween-20, Sigma), incubated (overnight, 4° C.) in blocking buffer (PBS-T, 5% Marvel) and subsequently incubated (2 h, room temperature) with the required primary antibody (see Table 4). After incubation with the primary antibody, membranes were further incubated (1 h, room temperature, 1 in 5000 dilution) with a horseradish peroxidase conjugated sheep anti-mouse (Clusterin and beta-actin, Amersham Pharmacia Biotech Ltd) or rabbit anti-goat secondary antibody (Jackson laboratories, Maine, USA). Thereafter, membranes were washed in PBS-T (6×15 min), incubated with the enhanced chemiluminescent assay reagent ECL-plus (Amersham Pharmacia Biotech Ltd) and the luminescent signal of the protein bands visualised using a Storm 860 scanner (Amersham Pharmacia Biotech Ltd).

TABLE 4

| Protein | Protein conc. (micrograms) | Acrylamide % in gel | Antibody | Antibody dilution v/v |
|---------|---------------------------|--------------------|----|------------------------|
| Clusterin precursor | 2.5 | 16 | Upstate anti-Clusterin (beta chain) (Cat No: 05-354) | 1 in 10,000 |
| Apolipo-protein A-IV precursor | 5 | 12 | C20, Santa Cruz anti-Apolipo-protein A-IV (recognising C- and N-terminal regions) (Cat No: SC-19038) | 1 in 1,000 |

TABLE 4-continued

| Protein | Protein conc. (micrograms) | Acrylamide % in gel | Antibody | Antibody dilution v/v |
|---------|---------------------------|--------------------|----|------------------------|
| Beta-actin | 300 | 12 | Sigma-Clone AC-74 (Cat No: A5316) | 1 in 250 |

Data and Statistical Analysis

Boxes of equal size were drawn around each band on Western blot images using ImageQuant (Amersham Pharmacia Biotech Ltd). The volume of all the pixels in each box was calculated, the background value subtracted and the remaining value anlaysed statistically, using the appropriate tests (Table 5). The Levene value (which tests whether the samples have equal variance) was determined for each group of data. If the Levene value was below 0.05 (samples have unequal variance), then the Welch statistic was checked and the Tamhane post hoc test was used. If the Levene value was above 0.05 then ANOVA was used with the Tukey HSD (Honestly Significant Difference) post hoc test.

After applying the appropriate post hoc test, a probability value (P) was obtained, less than 0.05 being considered significant.

It will be seen that a substantial number of significant or near-significant results (asterisked) at the P<0.05 level were obtained, including many between the moderate group and the control group and between the moderate group and the pre-symptomatic group.

Figure 3:
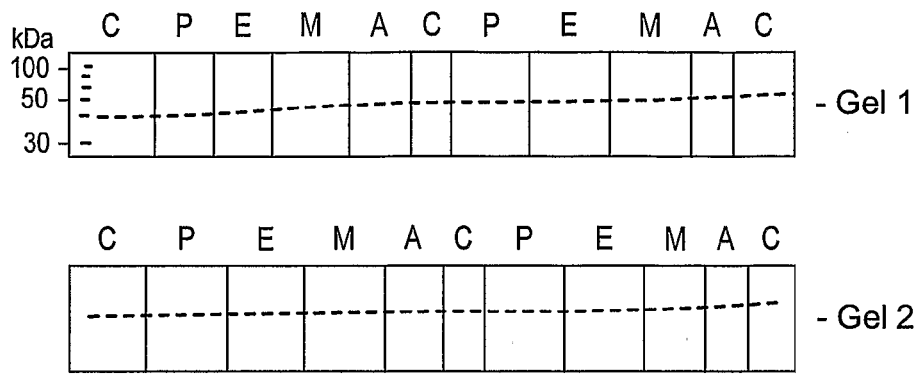
FIGS. 3, 4 and 5 show box and whisker plots of Western blotting results for a marker for HD, as more fully explained in Example 2.
Figure 3:
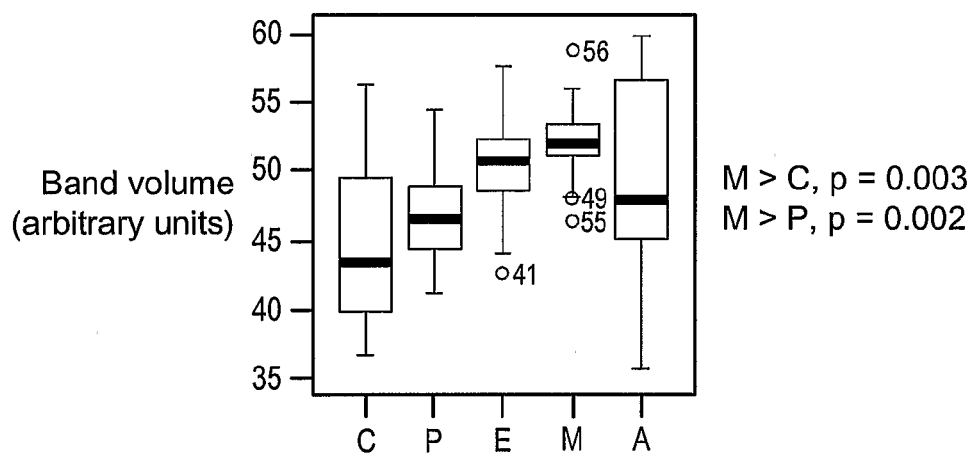
Figure 4:
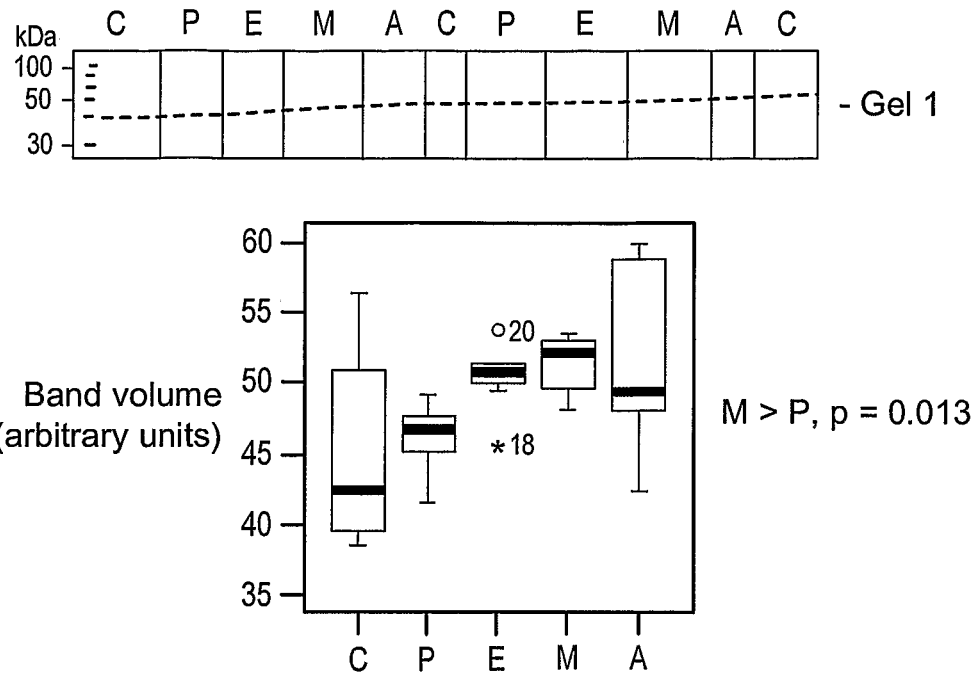
Figure 5:
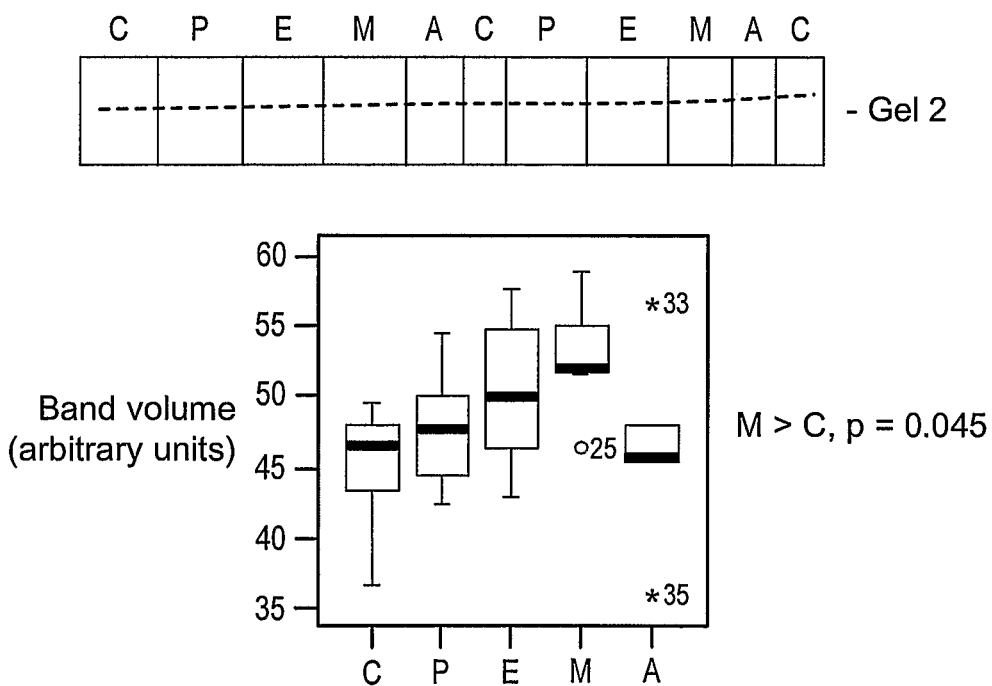

The results for one particular day were further analysed by box and whisker plots, for Gel 1 (35 results), Gel 2 (35 results) and Gels 1 & 2 (all 70 results). See FIGS. 3 to 5, where C=control, P=pre-symptomatic, E=early, M=moderate and A=advanced HD. The boxes represent the upper and lower quartiles above the median, denoted by the thick line, while the whiskers extend to the observations which are 1.5 times or less than the interquartile distance from the box. Outlier values, more than 1.5× and up to 3× the interquartile range, are shown as a circle, extreme cases, more than 3×, by an asterisk. The outliers and extreme cases were included in the statistical data analysis in Table 5. It will be seen that there was a substantial correlation between stage of the disease up to moderate and the density of the Clusterin precursor band on the gel.

TABLE 5

Statistical analysis of Clusterin precursor Western blots.

| Blot date | Gels | Levene | ANOVA | Welch | Post hoc | Group | P |
|-----------|------|--------|-------|-------|----------|-------|---|
| 31 Aug | 1 & 2 | 0.547 | 0.047 | 0.014 | Tukey HSD | A > C | 0.029 |
| 06 Sep | 1 & 2 | 0.002 | 0.075 | 0.006 | Tamhane | M > P | 0.041 |
|  |  |  |  |  |  | E > P | 0.03 |
| 08 Sep | 1 & 2 | 0.011 | 0.001 | 0.001 | Tamhane | M > C | 0.003 |
|  |  |  |  |  |  | M > P | 0.002 |
|  |  |  |  |  |  | E > C | 0.064* |
| 06 Sep | 1 | 0.069 | 0.004 | 0.023 | Tukey HSD | E > C | 0.005 |
|  |  |  |  |  |  | M > C | 0.011 |
| 07 Sep | 1 | 0.019 | 0.004 | 0.002 | Tamhane | A > P | 0.042 |
|  |  |  |  |  |  | M > P | 0.004 |
|  |  |  |  |  |  | A > C | 0.055* |
| 08 Sep | 1 | 0.00 | 0.029 | 0.013 | Tamhane | M > P | 0.013 |
|  |  |  |  |  |  | E > P | 0.089 |
| 06 Sep | 2 | 0.028 | 0.106 | 0.024 | Tamhane | A > P | 0.089* |
| 08 Sep | 2 | 0.766 | 0.044 | 0.051 | Tukey HSD | M > C | 0.045 |

*= nearly significant at P < 0.05.

Apolipoprotein A4 precursor was found to be significantly increased in moderate HD samples when compared to controls in one gel out of six (n=3, gel 1 and gel 2 experiments).

Beta-actin: the preliminary Western blots suggest that beta-actin is the protein that is changing in the 2D gel spot 1713. However, the blots had an extremely high background which inhibited quantification.

EXAMPLE 3

Introduction

Components within the plasma from patients with Huntingdon's disease (HD) and healthy controls (CON; not age-sex matched) were profiled using surface enhanced laser desorption/ionisation time-of flight mass spectrometry (SELDI). Three experiments were performed, each involving the same set of plasma samples but differing in the chip or wash buffer used. The HD group was further sub-divided into pre—(PRE), early—(EAR), moderate—(MOD) or advanced-disease (ADV). The control and disease groups all consisted of 15 patients samples except for the ADV group, which contained 10 samples. The protein profiles of plasma were obtained using Protein Chips (Ciphergen Biosystems) with either a strong anion exchange surface (SAX, Q10) or a weak cation exchange surface (WCX, CM10). The CM10 chips were equilibrated and washed in only one type of buffer whilst the Q10 chips were analysed following treatment with two alternative buffers. The experiment using Q10 chips washed in 100 mM Tris HCl (pH 9.0) is referred to as "Q10-Tris". The experiment involving Q10 chips washed in 50 mM sodium acetate (pH 6.5) is referred to as Q10-NaAc. The experiment involving CM10 chips washed in 50 mM ammonium acetate (pH 7.5) is referred to as CM10-AmAc.

Data Preparation

Calibration: The SELDI-TOF mass spectrometer was calibrated using a mixture of adrenocorticotropic hormone residues 18-39 (ACTH), cytochrome C, myoglobin and bovine serum albumin (BSA). Following acquisition of spectra for the protein profiling experiments, one spectrum was chosen as a reference spectrum (EAR sample 8117 in spot position E) and the corresponding spot over-layered with 1 μL of an aqueous solution containing the calibrant molecules. A further 1 μL of a 20 mg/mL solution of sinapinic acid (3,5-dimethoxy-4-hydroxycinnamic acid) matrix in 50% aqueous acetonitrile with 0.1% trifluoroacetic acid was added to the spot and allowed to dry for approximately 10 min. Spectra were acquired using the settings applied to the original samples and used to create calibration equations that were applied to the spectra, including the reference spectrum. The ions used to calibrate spectra were: singly-charged ACTH, m/z=2,466.72; doubly-charged cytochrome C, m/z=6, 181.05; doubly-charged myoglobin, m/z=8,476.78; singly-charged cytochrome C, m/z=12,361.10; singly-charged myoglobin, m/z=16,952.56; doubly-charged BSA, m/z=33, 216.00; singly-charged BSA, m/z=66,560.00). In call cases, average m/z values were used because the mass spectrometer was not able to resolve individual isotopic species. Separate calibration equations were produced for the low (2,467-16, 952) and high (16,952-66,560) m/z regions of the spectra and the m/z values of peaks in the spectra were assigned using the m/z values from the reference spectrum, calibrated in the appropriate m/z range. Masses referred to in the report are those derived from the calibrated reference spectra. The 95% confidence intervals (CI) of the average masses for the entire set of clinical samples are also given in Table 9. The 95% CI ranges of m/z values were estimated as the mean m/z value of all the matched peaks±two standard deviations. This range has a 95% probability of encompassing the true population mean m/z value and is a valid method of estimation due to the large (>100) number of samples used to derive the parameters of mean and standard deviation.

Peak marking: Peaks were manually marked using the tools provided by the ProteinChip software (Ciphergen Biosystems). Prior to peak marking, a baseline subtraction was performed using a fitted peak width of 5-times the expected peak width. For the Q10-Tris data set, a total of 71 peaks were marked across the m/z range 2,505-66,544. For the CM10-AmAc data set, 67 peaks were detected in the m/z range 2,509-65,587. For the Q10-NaAc data set, there were 66 peaks marked in the region 2,628-66,703. Following peak marking, a visual inspection of all spectra was made and the peak intensity data exported to Excel (Microsoft). The masses of matched peaks were checked in Excel and found to all have coefficients of variation of less than 0.90%. There were a small number of missing values in the data sets where peaks failed to be marked. These values were not converted to zeros but instead left as missing values.

Pre-processing: Quantile normalisation was performed according to the method of Bolstad et al. (2003) using a script written in the R statistical programming language (www.r-project.org). Prior to normalisation missing values were replaced with the mean peak intensity for spectra in the same group to provide a place-holder during the normalisation. Following normalisation, the place-holder values were converted back to missing values. Peak intensity data for peaks displaying positively-skewed distributions (skew>0.7) were $\log_{10}$ transformed prior to all data analysis.

Correlation Analysis

Pearson correlation coefficients were computed for replicate spectra. In the Q10-Tris data set, many of the samples were analysed in duplicate but some were analysed three times and some only once. Where duplicates existed, the correlation coefficient was computed for the pair. Where triplicates existed, three pair-wise correlation coefficients were computed. Where singlets existed, the mean correlation coefficient of that spectrum compared to all spectra was computed from the correlation matrix generated in the R environment. For the remaining data sets (CM10-AmAc and Q10-NaAc), the samples were analysed in duplicate and correlation coefficients were computed only for duplicate spectra. Prior to computing the correlation coefficients, the data were $\log_{10}$ transformed. This was done because there were many more peaks of low intensity than there were peaks of high intensity, so the correlation is more representative of the relationship between pairs of spectra after log transformation. The correlation data are shown in Table 6.

TABLE 6

Pearson Correlation of replicate samples in the Q10-Tris data set

| Group | Sample | Spot | Chip | Group | Sample | Spot | Chip | Replication | Correlation |
|---|---|---|---|---|---|---|---|---|---|
| EAR | 13342 | C | 5000 | EAR | 13342 | G | 5008 | Duplet | 0.98 |
| MOD | 10945 | A | 5008 | MOD | 10945 | C | 5011 | Duplet | 0.98 |
| EAR | 11262 | B | 5011 | EAR | 11262 | B | 5014 | Triplet | 0.97 |
| CON | 10653 | A | 5001 | CON | 10653 | E | 5015 | Duplet | 0.97 |
| EAR | 8117 | A | 5005 | EAR | 8117 | E | 5016 | Duplet | 0.97 |
| EAR | 8206 | A | 5003 | EAR | 8206 | H | 4998 | Duplet | 0.97 |
| MOD | 8131 | E | 5010 | MOD | 8131 | E | 5003 | Duplet | 0.97 |
| MOD | 8126 | C | 5017 | MOD | 8126 | H | 5005 | Duplet | 0.97 |
| EAR | 12112 | A | 5015 | EAR | 12112 | F | 4999 | Duplet | 0.97 |
| MOD | 13165 | B | 5005 | MOD | 13165 | C | 5001 | Duplet | 0.97 |
| CON | 8413 | A | 5016 | CON | 8413 | E | 5002 | Duplet | 0.97 |
| EAR | 11262 | B | 5011 | EAR | 11262 | B | 5013 | Triplet | 0.97 |
| EAR | 10837 | B | 5001 | EAR | 10837 | H | 5001 | Duplet | 0.96 |
| ADV | 13272 | E | 5005 | ADV | 13272 | F | 4998 | Duplet | 0.96 |
| CON | 11207 | G | 5011 | CON | 11207 | G | 5007 | Duplet | 0.96 |
| EAR | 11298 | H | 5014 | EAR | 11298 | D | 5003 | Triplet | 0.96 |
| CON | 8358 | A | 5007 | CON | 8358 | C | 5006 | Duplet | 0.96 |
| CON | 10841 | B | 5000 | CON | 10841 | F | 5008 | Duplet | 0.96 |
| CON | 8114 | C | 5018 | CON | 8114 | E | 4999 | Duplet | 0.96 |
| EAR | 8355 | B | 4998 | EAR | 8355 | H | 5007 | Duplet | 0.96 |

TABLE 6-continued

Pearson Correlation of replicate samples in the Q10-Tris data set

| Group | Sample | Spot | Chip | Group | Sample | Spot | Chip | Replication | Correlation |
|---|---|---|---|---|---|---|---|---|---|
| ADV | 13164 | F | 5011 | ADV | 13164 | F | 5001 | Duplet | 0.96 |
| CON | 10947 | C | 5003 | CON | 10947 | G | 5017 | Duplet | 0.96 |
| MOD | 10866 | A | 4999 | MOD | 10866 | A | 5012 | Duplet | 0.96 |
| MOD | 10843 | C | 5007 | MOD | 10843 | D | 5000 | Duplet | 0.96 |
| PRE | 12323 | D | 5004 | PRE | 12323 | F | 5018 | Duplet | 0.96 |
| MOD | 10868 | C | 5004 | MOD | 10868 | G | 4999 | Duplet | 0.96 |
| ADV | 11841 | F | 5007 | ADV | 11841 | H | 5006 | Duplet | 0.96 |
| MOD | 8119 | B | 5015 | MOD | 8119 | H | 5008 | Duplet | 0.96 |
| PRE | 12575 | E | 5000 | PRE | 12575 | F | 5010 | Duplet | 0.96 |
| EAR | 11262 | B | 5013 | EAR | 11262 | B | 5014 | Triplet | 0.96 |
| EAR | 11289 | D | 5006 | EAR | 11289 | H | 5011 | Duplet | 0.96 |
| MOD | 12492 | E | 5018 | MOD | 12492 | G | 5002 | Duplet | 0.96 |
| EAR | 11298 | H | 5014 | EAR | 11298 | H | 5013 | Triplet | 0.95 |
| MOD | 8125 | A | 5018 | MOD | 8125 | F | 5016 | Duplet | 0.95 |
| PRE | 12581 | C | 5015 | PRE | 12581 | C | 5005 | Duplet | 0.95 |
| PRE | 11260 | B | 4999 | PRE | 11260 | B | 5002 | Duplet | 0.95 |
| ADV | 8113 | B | 5006 | ADV | 8113 | D | 5002 | Duplet | 0.95 |
| EAR | 8116 | B | 5017 | EAR | 8116 | F | 5012 | Duplet | 0.95 |
| ADV | 8201 | H | 5010 | ADV | 8201 | H | 4997 | Duplet | 0.95 |
| PRE | 12360 | B | 5008 | PRE | 12360 | H | 4999 | Duplet | 0.95 |
| CON | 10969 | A | 5017 | CON | 10969 | H | 5004 | Duplet | 0.94 |
| ADV | 8391 | D | 5012 | ADV | 8391 | D | 4999 | Duplet | 0.94 |
| MOD | 8144 | B | 5016 | MOD | 8144 | G | 5012 | Duplet | 0.94 |
| CON | 13166 | A | 5011 | CON | 13166 | E | 5012 | Duplet | 0.94 |
| CON | 8421 | G | 5014 | CON | 8421 | G | 4998 | Triplet | 0.94 |
| EAR | 11205 | D | 5010 | EAR | 11205 | H | 5017 | Duplet | 0.94 |
| PRE | 12127 | D | 5007 | PRE | 12127 | H | 5015 | Duplet | 0.94 |
| PRE | 13262 | G | 5016 | PRE | 13262 | H | 5012 | Duplet | 0.94 |
| EAR | 12363 | D | 5018 | EAR | 12363 | F | 5002 | Duplet | 0.94 |
| PRE | 11294 | C | 5016 | PRE | 11294 | F | 5003 | Duplet | 0.94 |
| MOD | 10835 | C | 5013 | MOD | 10835 | G | 5015 | Duplet | 0.93 |
| PRE | 8115 | B | 5012 | PRE | 8115 | D | 5014 | Triplet | 0.93 |
| CON | 8416 | D | 5016 | CON | 8416 | B | 4997 | Duplet | 0.93 |
| PRE | 13159 | A | 5010 | PRE | 13159 | D | 5017 | Duplet | 0.93 |
| EAR | 11298 | D | 5003 | EAR | 11298 | H | 5013 | Triplet | 0.93 |
| MOD | 8192 | E | 5006 | MOD | 8192 | D | 4997 | Duplet | 0.93 |
| CON | 8421 | G | 5013 | CON | 8421 | G | 5014 | Triplet | 0.93 |
| PRE | 8115 | B | 5012 | PRE | 8115 | D | 5013 | Triplet | 0.93 |
| CON | 8421 | G | 5013 | CON | 8421 | G | 4998 | Triplet | 0.92 |
| PRE | 8115 | D | 5014 | PRE | 8115 | D | 5013 | Triplet | 0.91 |
| PRE | 13158 | D | 5011 | PRE | 13158 | H | 5002 | Duplet | 0.91 |
| PRE | 13266 | B | 5018 | PRE | 13266 | D | 5001 | Duplet | 0.91 |
| EAR | 11924 | B | 5004 | EAR | 11924 | F | 5015 | Duplet | 0.90 |
| CON | 8423 | A | 5004 | CON | 8423 | A | 5013 | Triplet | 0.89 |
| PRE | 12317 | D | 4998 | PRE | 12317 | E | 4997 | Duplet | 0.88 |
| CON | 8423 | A | 5004 | CON | 8423 | A | 5014 | Triplet | 0.88 |
| CON | 8423 | A | 5013 | CON | 8423 | A | 5014 | Triplet | 0.87 |
| ADV | 8361 | G | 5004 | ADV | 8361 | H | 5003 | Duplet | 0.87 |
| ADV | 13391 | B | 5003 | ADV | 13391 | B | 5010 | Duplet | 0.86 |
| CON | 8198 | G | 5001 | | Not-replicated | | | Singlet | 0.84 |
| MOD | 8195 | A | 5014 | | Not-replicated | | | Singlet | 0.84 |
| EAR | 10651 | B | 5007 | EAR | 10651 | C | 4997 | Duplet | 0.83 |
| PRE | 8227 | A | 5006 | | Not-replicated | | | Singlet | 0.82 |
| CON | 13161 | C | 5010 | CON | 13161 | F | 5005 | Duplet | 0.81 |
| ADV | 8120 | E | 5008 | ADV | 8120 | A | 4997 | Duplet | 0.81 |
| MOD | 8386 | C | 4998 | | Not-replicated | | | Singlet | 0.77 |
| CON | 10739 | A | 4998 | | Not-replicated | | | Singlet | 0.77 |
| EAR | 8142 | G | 5005 | | Not-replicated | | | Singlet | 0.77 |
| PRE | 8118 | F | 5006 | | Not-replicated | | | Singlet | 0.76 |
| ADV | 13271 | A | 5000 | ADV | 13271 | H | 5000 | Duplet | 0.54 |

Figure 6:
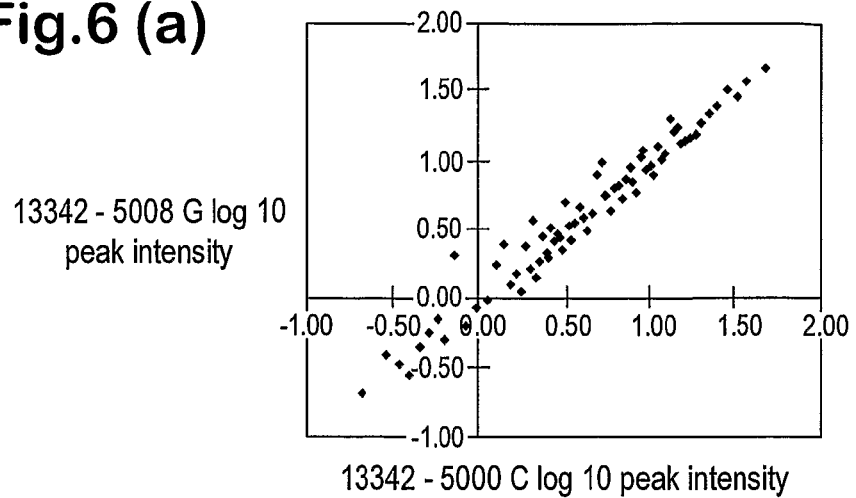
FIG. 6 shows scatter-plots of replicate spectra from the Q10-Tris data set as explained in Example 3.
Figure 6:
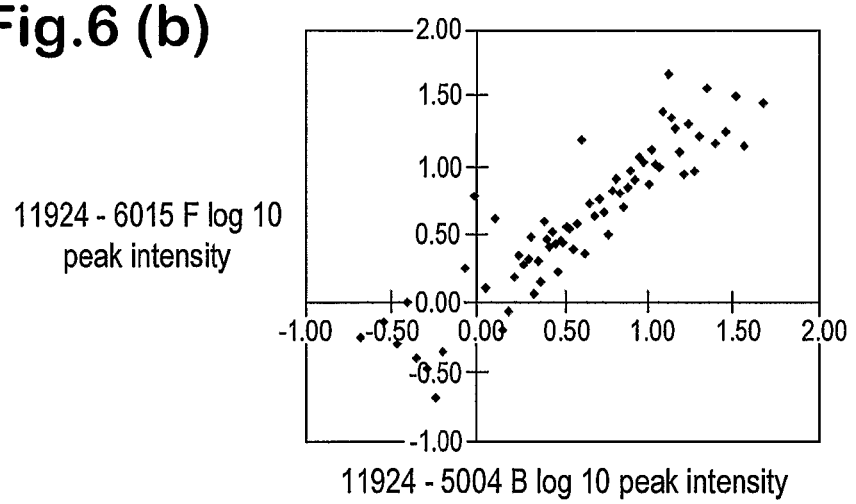
Figure 6:
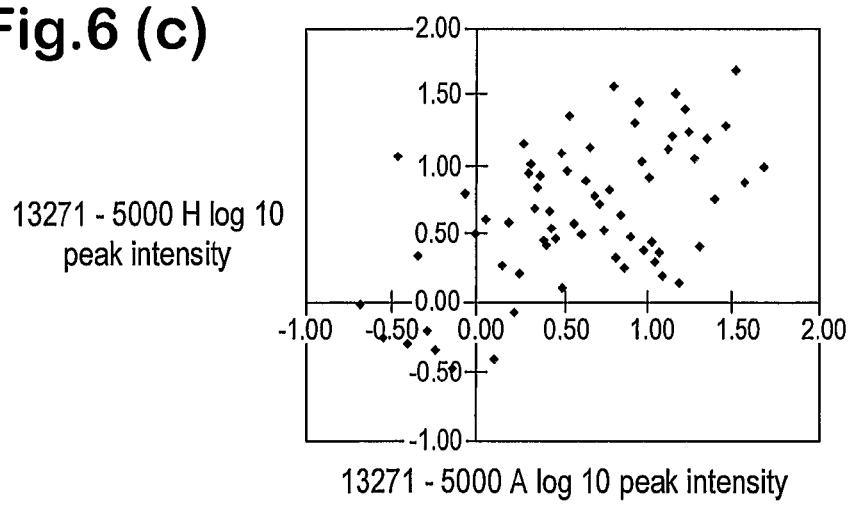

The results of the correlation analysis of the Q10-Tris data set indicated that the majority of the replicate spectra were very similar. Indeed, 63 of the 80 comparisons resulted in values of r≧0.9. Of the 17 comparisons of replicate spectra that gave values of r<0.9, seven were mean values of r for the non-replicated (singlet) spectra compared to the other spectra in the correlation matrix and these would perhaps be expected to be less than the direct comparisons of replicate spectra. Of the remaining 10 duplicate spectra that were correlated with r<0.9, only one was particularly suspicious. The duplicates of sample 13271 were correlated with r=0.54. Closer inspection of this pair suggested that the spectrum acquired from position H of chip 5000 was visually dissimilar to the other spectra in the experiment and so this spectrum was excluded. The mean value of r across the correlation matrix for the remaining sample 13271 was 0.75, in line with mean values of the other non-replicated samples. FIG. 6 shows scatterplots of three replicate spectra in the Q10-Tris data set with correlation coefficients of 0.98 (1a), 0.90 (1b) and 0.54 (1c). In particular, the plots are:

a) Duplicate spectra of sample 13342. The correlation coefficient of this pair is 0.98.

b) Duplicate spectra of sample 11924. The correlation coefficient of this pair is 0.90.
c) Duplicate spectra of sample 13271. The correlation coefficient of this pair is 0.54.

The correlations of replicate spectra in the CM10-AmAc and Q10-NaAc data sets involved only duplicate spectra and the Pearson correlation values are given in Tables 7 and 8, respectively.

TABLE 7

Pearson Correlation of replicate samples in the CM10-AmAc data set

| Group | Sample | Spot | Chip | Group | Sample | Spot | Chip | Correlation |
|---|---|---|---|---|---|---|---|---|
| ADV | 8113 | B | 1419 | ADV | 8113 | D | 1415 | 0.98 |
| ADV | 8391 | D | 1616 | ADV | 8391 | D | 1412 | 0.97 |
| ADV | 8120 | A | 1410 | ADV | 8120 | E | 1421 | 0.97 |
| EAR | 11262 | B | 1615 | EAR | 11262 | B | 1617 | 0.96 |
| CON | 10947 | C | 1416 | CON | 10947 | G | 1621 | 0.96 |
| ADV | 8361 | G | 1417 | ADV | 8361 | H | 1416 | 0.96 |
| MOD | 13165 | B | 1418 | MOD | 13165 | C | 1414 | 0.96 |
| PRE | 13266 | B | 1622 | PRE | 13266 | D | 1414 | 0.96 |
| PRE | 13262 | G | 1620 | PRE | 13262 | H | 1616 | 0.96 |
| MOD | 10835 | C | 1617 | MOD | 10835 | G | 1619 | 0.96 |
| MOD | 8119 | B | 1619 | MOD | 8119 | H | 1421 | 0.96 |
| CON | 8416 | B | 1410 | CON | 8416 | D | 1620 | 0.96 |
| ADV | 11841 | F | 1420 | ADV | 11841 | H | 1419 | 0.96 |
| MOD | 8131 | E | 1614 | MOD | 8131 | E | 1416 | 0.96 |
| MOD | 10945 | A | 1421 | MOD | 10945 | C | 1615 | 0.95 |
| PRE | 8227 | A | 1419 | PRE | 8227 | G | 1618 | 0.95 |
| EAR | 10837 | B | 1414 | EAR | 10837 | H | 1414 | 0.95 |
| ADV | 8201 | H | 1614 | ADV | 8201 | H | 1410 | 0.95 |
| PRE | 12581 | C | 1619 | PRE | 12581 | C | 1418 | 0.95 |
| EAR | 13342 | C | 1413 | EAR | 13342 | G | 1421 | 0.95 |
| EAR | 11924 | B | 1417 | EAR | 11924 | F | 1619 | 0.94 |
| PRE | 12323 | D | 1417 | PRE | 12323 | F | 1622 | 0.94 |
| MOD | 8126 | C | 1621 | MOD | 8126 | H | 1418 | 0.94 |
| MOD | 8144 | B | 1620 | MOD | 8144 | G | 1616 | 0.94 |
| PRE | 12360 | B | 1421 | PRE | 12360 | H | 1412 | 0.94 |
| CON | 8421 | G | 1617 | CON | 8421 | G | 1411 | 0.94 |
| PRE | 8118 | B | 1618 | PRE | 8118 | F | 1419 | 0.94 |
| EAR | 8142 | E | 1618 | EAR | 8142 | G | 1418 | 0.94 |
| MOD | 10866 | A | 1412 | MOD | 10866 | A | 1616 | 0.93 |
| EAR | 11298 | D | 1416 | EAR | 11298 | H | 1617 | 0.93 |
| CON | 10653 | A | 1414 | CON | 10653 | E | 1619 | 0.93 |
| CON | 8413 | A | 1620 | CON | 8413 | E | 1415 | 0.93 |
| PRE | 13159 | A | 1614 | PRE | 13159 | D | 1621 | 0.93 |
| PRE | 11260 | B | 1412 | PRE | 11260 | B | 1415 | 0.93 |
| EAR | 10651 | B | 1420 | EAR | 10651 | C | 1410 | 0.93 |
| MOD | 8125 | A | 1622 | MOD | 8125 | F | 1620 | 0.93 |
| MOD | 8192 | D | 1410 | MOD | 8192 | E | 1419 | 0.93 |
| ADV | 13164 | F | 1615 | ADV | 13164 | F | 1414 | 0.93 |
| CON | 10969 | A | 1621 | CON | 10969 | H | 1417 | 0.93 |
| PRE | 12575 | E | 1413 | PRE | 12575 | F | 1614 | 0.93 |
| MOD | 10868 | C | 1417 | MOD | 10868 | G | 1412 | 0.92 |
| EAR | 8116 | B | 1621 | EAR | 8116 | F | 1616 | 0.92 |
| CON | 11207 | G | 1615 | CON | 11207 | G | 1420 | 0.92 |
| PRE | 12317 | D | 1411 | PRE | 12317 | E | 1410 | 0.92 |
| PRE | 8115 | B | 1616 | PRE | 8115 | D | 1617 | 0.92 |
| EAR | 12363 | D | 1622 | EAR | 12363 | F | 1415 | 0.92 |
| MOD | 8195 | A | 1415 | MOD | 8195 | A | 1418 | 0.92 |
| PRE | 12127 | D | 1420 | PRE | 12127 | H | 1619 | 0.92 |
| ADV | 13271 | A | 1413 | ADV | 13271 | H | 1413 | 0.91 |
| MOD | 10843 | C | 1420 | MOD | 10843 | D | 1413 | 0.91 |
| EAR | 11289 | D | 1419 | EAR | 11289 | H | 1615 | 0.91 |
| EAR | 11205 | D | 1614 | EAR | 11205 | H | 1621 | 0.91 |
| EAR | 8117 | A | 1418 | EAR | 8117 | E | 1620 | 0.91 |
| EAR | 12112 | A | 1619 | EAR | 12112 | F | 1412 | 0.90 |
| CON | 10739 | A | 1411 | CON | 10739 | D | 1618 | 0.90 |
| CON | 8114 | C | 1622 | CON | 8114 | E | 1412 | 0.90 |
| PRE | 13158 | D | 1615 | PRE | 13158 | H | 1415 | 0.89 |
| CON | 8198 | G | 1414 | CON | 8198 | H | 1618 | 0.89 |
| ADV | 13272 | E | 1418 | ADV | 13272 | F | 1411 | 0.89 |
| CON | 8423 | A | 1417 | CON | 8423 | A | 1617 | 0.88 |
| MOD | 12492 | E | 1622 | MOD | 12492 | G | 1415 | 0.88 |
| CON | 13166 | A | 1615 | CON | 13166 | E | 1616 | 0.88 |
| MOD | 8386 | C | 1411 | MOD | 8386 | F | 1618 | 0.88 |
| CON | 8358 | A | 1420 | CON | 8358 | C | 1419 | 0.87 |
| CON | 13161 | C | 1614 | CON | 13161 | F | 1418 | 0.87 |
| EAR | 8206 | A | 1416 | EAR | 8206 | H | 1411 | 0.87 |
| EAR | 8355 | B | 1411 | EAR | 8355 | H | 1420 | 0.87 |
| PRE | 11294 | C | 1620 | PRE | 11294 | F | 1416 | 0.87 |

TABLE 7-continued

Pearson Correlation of replicate samples in the CM10-AmAc data set

| Group | Sample | Spot | Chip | Group | Sample | Spot | Chip | Correlation |
|---|---|---|---|---|---|---|---|---|
| CON | 10841 | B | 1413 | CON | 10841 | F | 1421 | 0.85 |
| ADV | 13391 | B | 1416 | ADV | 13391 | B | 1614 | 0.84 |

TABLE 8

Pearson Correlation of replicate samples in the Q10-NaAc data set

| Group | Sample | Spot | Chip | Group | Sample | Spot | Chip | Correlation |
|---|---|---|---|---|---|---|---|---|
| EAR | 11262 | B | 4974 | EAR | 11262 | B | 4976 | 0.99 |
| PRE | 8115 | B | 4975 | PRE | 8115 | D | 4976 | 0.98 |
| MOD | 8144 | B | 5360 | MOD | 8144 | G | 4975 | 0.98 |
| EAR | 8116 | B | 4980 | EAR | 8116 | F | 4975 | 0.98 |
| ADV | 8113 | B | 6514 | ADV | 8113 | D | 6510 | 0.98 |
| PRE | 13159 | A | 4973 | PRE | 13159 | D | 4980 | 0.98 |
| CON | 10841 | B | 6508 | CON | 10841 | F | 6516 | 0.98 |
| MOD | 8192 | D | 6505 | MOD | 8192 | E | 6514 | 0.98 |
| CON | 10739 | A | 6506 | CON | 10739 | D | 4977 | 0.97 |
| EAR | 12363 | D | 4981 | EAR | 12363 | F | 6510 | 0.97 |
| MOD | 10835 | C | 4976 | MOD | 10835 | G | 4978 | 0.97 |
| MOD | 10866 | A | 6507 | MOD | 10866 | A | 4975 | 0.97 |
| ADV | 11841 | F | 6515 | ADV | 11841 | H | 6514 | 0.97 |
| ADV | 8361 | G | 6502 | ADV | 8361 | H | 6511 | 0.97 |
| MOD | 8126 | C | 4980 | MOD | 8126 | H | 6513 | 0.97 |
| CON | 8198 | G | 6509 | CON | 8198 | H | 4977 | 0.97 |
| PRE | 11294 | C | 5360 | PRE | 11294 | F | 6511 | 0.97 |
| EAR | 10651 | B | 6515 | EAR | 10651 | C | 6505 | 0.97 |
| CON | 8416 | B | 6505 | CON | 8416 | D | 5360 | 0.97 |
| PRE | 13158 | D | 4974 | PRE | 13158 | H | 6510 | 0.97 |
| MOD | 13165 | B | 6513 | MOD | 13165 | C | 6509 | 0.96 |
| MOD | 8386 | C | 6506 | MOD | 8386 | F | 4977 | 0.96 |
| CON | 11207 | G | 4974 | CON | 11207 | G | 6515 | 0.96 |
| EAR | 12112 | A | 4978 | EAR | 12112 | F | 6507 | 0.96 |
| PRE | 8227 | A | 6514 | PRE | 8227 | G | 4977 | 0.96 |
| MOD | 10843 | C | 6515 | MOD | 10843 | D | 6508 | 0.96 |
| ADV | 13271 | A | 6508 | ADV | 13271 | H | 6508 | 0.96 |
| CON | 8114 | C | 4981 | CON | 8114 | E | 6507 | 0.96 |
| CON | 8358 | A | 6515 | CON | 8358 | C | 6514 | 0.96 |
| CON | 10969 | A | 4980 | CON | 10969 | H | 6502 | 0.96 |
| MOD | 8125 | A | 4981 | MOD | 8125 | F | 5360 | 0.96 |
| EAR | 8117 | A | 6513 | EAR | 8117 | E | 5360 | 0.96 |
| MOD | 8131 | E | 4973 | MOD | 8131 | E | 6511 | 0.96 |
| ADV | 13164 | F | 4974 | ADV | 13164 | F | 6509 | 0.95 |
| PRE | 12575 | E | 6508 | PRE | 12575 | F | 4973 | 0.95 |
| CON | 8421 | G | 4976 | CON | 8421 | G | 6506 | 0.95 |
| PRE | 12317 | D | 6506 | PRE | 12317 | E | 6505 | 0.95 |
| ADV | 8201 | H | 4973 | ADV | 8201 | H | 6505 | 0.95 |
| CON | 8423 | A | 6502 | CON | 8423 | A | 4976 | 0.95 |
| PRE | 12360 | B | 6516 | PRE | 12360 | H | 6507 | 0.95 |
| PRE | 13262 | G | 5360 | PRE | 13262 | H | 4975 | 0.94 |
| ADV | 8120 | A | 6505 | ADV | 8120 | E | 6516 | 0.94 |
| CON | 13166 | A | 4974 | CON | 13166 | E | 4975 | 0.94 |
| EAR | 11298 | D | 6511 | EAR | 11298 | H | 4976 | 0.94 |
| EAR | 8206 | A | 6511 | EAR | 8206 | H | 6506 | 0.94 |
| EAR | 11924 | B | 6502 | EAR | 11924 | F | 4978 | 0.94 |
| CON | 8413 | A | 5360 | CON | 8413 | E | 6510 | 0.94 |
| EAR | 11205 | D | 4973 | EAR | 11205 | H | 4980 | 0.94 |
| PRE | 11260 | B | 6507 | PRE | 11260 | B | 6510 | 0.93 |
| MOD | 10945 | A | 6516 | MOD | 10945 | C | 4974 | 0.93 |
| EAR | 10837 | B | 6509 | EAR | 10837 | H | 6509 | 0.93 |
| MOD | 12492 | E | 4981 | MOD | 12492 | G | 6510 | 0.93 |
| MOD | 8119 | B | 4978 | MOD | 8119 | H | 6516 | 0.93 |
| PRE | 12127 | D | 6515 | PRE | 12127 | H | 4978 | 0.93 |
| CON | 10653 | A | 6509 | CON | 10653 | E | 4978 | 0.93 |
| EAR | 11289 | D | 6514 | EAR | 11289 | H | 4974 | 0.92 |
| MOD | 8195 | A | 6510 | MOD | 8195 | A | 4977 | 0.92 |
| ADV | 13272 | E | 6513 | ADV | 13272 | F | 6506 | 0.92 |
| CON | 13161 | C | 4973 | CON | 13161 | F | 6513 | 0.91 |
| EAR | 8355 | B | 6506 | EAR | 8355 | H | 6515 | 0.91 |
| MOD | 10868 | C | 6502 | MOD | 10868 | G | 6507 | 0.91 |
| PRE | 13266 | B | 4981 | PRE | 13266 | D | 6509 | 0.90 |
| PRE | 12581 | C | 4978 | PRE | 12581 | C | 6513 | 0.90 |
| ADV | 13391 | B | 6511 | ADV | 13391 | B | 4973 | 0.89 |

TABLE 8-continued

Pearson Correlation of replicate samples in the Q10-NaAc data set

| Group | Sample | Spot | Chip | Group | Sample | Spot | Chip | Correlation |
|---|---|---|---|---|---|---|---|---|
| PRE | 12323 | D | 6502 | PRE | 12323 | F | 4981 | 0.88 |
| ADV | 8391 | D | 4975 | ADV | 8391 | D | 6507 | 0.87 |
| EAR | 13342 | C | 6508 | EAR | 13342 | G | 6516 | 0.87 |
| EAR | 8142 | E | 4977 | EAR | 8142 | G | 6513 | 0.85 |
| PRE | 8118 | B | 4977 | PRE | 8118 | F | 6514 | 0.83 |

In the CM10-AmAc data set, the values of Pearson correlation values for the duplicate spectra ranged from 0.98 to 0.84, with 56 of the 70 duplicates being correlated with $r \geq 0.90$. In the Q10-NaAc data set, the Pearson correlation values ranged from 0.99 to 0.83, with 63 of the 69 duplicates being correlated with $r \geq 0.90$. No spectra were excluded from these data sets on the basis of the correlation analysis.

Averaging: To improve the reliability of the measurements of peaks in the SELDI profiles, averages (means) were calculated from the available replicates. This has previously been shown in our laboratory to improve correlations between a set of spectra comprising biological replicates when averages of pairs are taken to represent the sample. For the data analysis, averaged data were used in place of the original replicates. This is particularly important because it avoids giving an over-estimate of the degrees of freedom in the statistical hypothesis tests, as would occur when replicate samples are used as if they were independent biological samples.

Statistical Hypothesis Testing

Several related methods were used for univariate data analysis of the quantile normalised and averaged data set. These can broadly be divided into tests for the assumption that all the means are equal, and multiple comparisons procedures that test the equality of the means of individual pairs of groups. Additionally, a test for homogeneity of variances was performed before testing the means to determine the appropriate set of tests to perform.

In order to test the important assumption of ANOVA that the groups have equal variance, Levene's test was used at the 95% level. If Levene's test returned a p-value of >0.05, the alternative hypothesis was rejected and the groups were assumed to have equal variance. When equal variance was assumed, one-way ANOVA was used to test the equality of group means. When equal variance could not be assumed (i.e. when Levene's test returned a p-value of <0.05) Welch's test for equality of means was used as a more robust alternative. Both the one-way ANOVA and Welch's test were preformed at the 95% level.

When the group means were found to be unequal, one of two tests were used to test all pairs of groups in the data sets. If the means were found to be unequal using the one-way ANOVA test, Tukey's honestly significant difference (HSD) was used to compare all groups. If the means were found to be unequal using Welch's test, then Tamhane's T2 was employed to compare all groups. Both multiple comparisons methods were performed at the 95% level.

Table 9 shows information relating to the peaks found to have statistically significant differences in the means of the five groups (CON, PRE, EAR, MOD and ADV).

TABLE 9

Peaks found to be statistically different in the Q10-Tris, Q10-NaAc or CM10-AmAc data sets using the univariate tests.

| Master Peak No. | Data set | Peak m/z | Peak m/z 95% CI | Equality of means | Group differences |
|---|---|---|---|---|---|
| 1 | Q10-Tris | 3564.76 | 3555.50-3574.22 | 0.018[a] | CON ≠ ADV (1.25-fold decreased in ADV) |
| | | | | | PRE ≠ ADV (1.27-fold decreased in ADV) |
| 2 | CM10-AmAc | 3662.78 | 3656.58-3679.43 | 0.002[a] | CON ≠ ADV (1.57-fold decreased in ADV) |
| | | | | | PRE ≠ ADV (1.37-fold decreased in ADV) |
| | | | | | EAR ≠ ADV (1.51-fold decreased in ADV) |
| | | | | | MOD ≠ ADV (1.48-fold decreased in ADV) |
| 3 | CM10-AmAc | 4227.05 | 4206.08-4228.74 | 0.040[a] | PRE ≠ ADV (1.74-fold decreased in ADV) |
| 4 | Q10-NaAc | 4296.42 | 4287.60-4301.56 | 0.011[a] | PRE ≠ ADV (3.85-fold decreased in ADV) |
| 5 | Q10-NaAc | 4357.75 | 4351.19-4364.63 | 0.023[a] | CON ≠ ADV (1.90-fold decreased in ADV) |
| | | | | | PRE ≠ ADV (1.95-fold decreased in ADV) |
| 6 | Q10-Tris | 4371.83 | 4360.58-4376.90 | 0.047[a] | CON ≠ ADV (1.38-fold increased in ADV) |
| 7 | Q10-Tris | 4479.08 | 4471.89-4481.98 | 0.013[b] | CON ≠ ADV (1.78-fold increased in ADV) |
| 8 | Q10-NaAc | 4720.37 | 4716.23-4724.48 | 0.000[a] | CON ≠ ADV (2.09-fold decreased in ADV) |
| | | | | | PRE ≠ ADV (1.91-fold decreased in ADV) |
| | | | | | EAR ≠ ADV (1.87-fold decreased in ADV) |
| | | | | | MOD ≠ ADV (2.06-fold decreased in ADV) |
| 8 | Q10-Tris | 4721.02 | 4710.43-4726.35 | 0.007[b] | CON ≠ ADV (1.33-fold decreased in ADV) |
| | | | | | MOD ≠ ADV (1.52-fold decreased in ADV) |
| 9 | Q10-NaAc | 5760.90 | 5751.18-5778.87 | 0.035[a] | EAR ≠ ADV (1.57-fold decreased in ADV) |
| 10 | CM10-AmAc | 5966.63 | 5960.49-5981.23 | 0.005[a] | CON ≠ EAR (1.31-fold increased in EAR) |
| | | | | | MOD ≠ EAR (1.35-fold increased in EAR) |
| 11 | Q10-NaAc | 6523.63 | 6515.57-6540.55 | 0.046[b] | PRE ≠ ADV (3.29-fold decreased in ADV) |
| 12 | CM10-AmAc | 6919.51 | 6913.11-6927.14 | 0.018[a] | CON ≠ EAR (1.16-fold decreased in EAR) |
| 13 | Q10-NaAc | 6985.41 | 6983.66-7011.20 | 0.008[a] | CON ≠ ADV (2.54-fold decreased in ADV) |
| | | | | | PRE ≠ ADV (2.62-fold decreased in ADV) |
| | | | | | EAR ≠ ADV (2.32-fold decreased in ADV) |
| | | | | | MOD ≠ ADV (2.37-fold decreased in ADV) |

TABLE 9-continued

Peaks found to be statistically different in the Q10-Tris, Q10-NaAc or CM10-AmAc data sets using the univariate tests.

| Master Peak No. | Data set | Peak m/z | Peak m/z 95% CI | Equality of means | Group differences |
|---|---|---|---|---|---|
| 14 | CM10-AmAc | 7034.90 | 7030.01-7043.33 | 0.008[a] | CON ≠ ADV (1.48-fold decreased in ADV)<br>PRE ≠ ADV (1.54-fold decreased in ADV)<br>EAR ≠ ADV (1.47-fold decreased in ADV)<br>MOD≠ ADV (1.42-fold decreased in ADV) |
| 15 | CM10-AmAc | 7080.59 | 7067.18-7087.69 | 0.007[a] | CON ≠ ADV (1.39-fold decreased in ADV)<br>PRE ≠ ADV (1.38-fold decreased in ADV)<br>EAR ≠ ADV (1.38-fold decreased in ADV)<br>MOD≠ ADV (2.08-fold decreased in ADV) |
| 16 | Q10-NaAc | 7624.59 | 7605.45-7637.52 | 0.005[b] | MOD ≠ ADV (1.48-fold decreased in ADV) |
| 17 | CM10-AmAc | 8139.10 | 8133.70-8149.02 | 0.005[a] | CON ≠ ADV (1.85-fold increased in ADV)<br>PRE ≠ ADV (2.17-fold increased in ADV)<br>EAR ≠ ADV (1.88-fold increased in ADV)<br>MOD≠ ADV (2.08-fold increased in ADV) |
| 18 | CM10-AmAc | 8208.41 | 8204.81-8224.70 | 0.016[a] | CON ≠ ADV (1.87-fold increased in ADV)<br>PRE ≠ ADV (1.92-fold increased in ADV)<br>MOD≠ ADV (1.97-fold increased in ADV) |
| 19 | CM10-AmAc | 8251.49 | 8228.44-8251.50 | 0.001[b] | CON ≠ ADV (2.00-fold increased in ADV)<br>PRE ≠ ADV (2.07-fold increased in ADV)<br>EAR ≠ ADV (1.72-fold increased in ADV)<br>MOD≠ ADV (2.44-fold increased in ADV) |
| 20 | Q10-NaAc | 8466.00 | 8456.99-8472.79 | 0.013[b] | CON ≠ ADV (4.32-fold decreased in ADV)<br>$(p < 0.15)$[c] |
| 21 | Q10-NaAc | 8763.16 | 8760.65-8775.33 | 0.030[b] | CON ≠ ADV (1.59-fold decreased in ADV)<br>PRE ≠ ADV (1.71-fold decreased in ADV)<br>EAR ≠ ADV (1.70-fold decreased in ADV)<br>MOD≠ ADV (1.67-fold decreased in ADV)<br>$(p < 0.20)$[c] |
| 22 | Q10-NaAc | 9135.76 | 9124.91-9140.55 | 0.028[b] | MOD ≠ ADV (3.59-fold decreased in ADV) |
| 23 | Q10-NaAc | 9632.25 | 9624.52-9652.90 | 0.027[b] | CON ≠ ADV (2.81-fold decreased in ADV)<br>MOD ≠ ADV (2.77-fold decreased in ADV) |
| 24 | Q10-NaAc | 9936.86 | 9912.33-9946.84 | 0.035[b] | EAR ≠ ADV (1.94-fold decreased in ADV)<br>MOD≠ ADV (1.80-fold decreased in ADV)<br>$(p < 0.19)$[c] |
| 25 | Q10-NaAc | 10450.60 | 10425.49-10476.21 | 0.039[b] | EAR ≠ ADV (1.85-fold decreased in ADV)<br>MOD≠ ADV (1.61-fold decreased in ADV)<br>$(p < 0.13)$[c] |
| 26 | Q10-Tris | 11533.31 | 11496.71-11559.00 | 0.020[a] | PRE ≠ ADV (2.59-fold increased in ADV)<br>MOD ≠ ADV (2.32-fold increased in ADV) |
| 27 | CM10-AmAc | 15964.13 | 15943.28-15988.41 | 0.004[a] | CON ≠ ADV (1.94-fold increased in ADV)<br>PRE ≠ ADV (2.22-fold increased in ADV)<br>EAR ≠ ADV (2.03-fold increased in ADV)<br>MOD≠ ADV (2.07-fold increased in ADV) |
| 28 | CM10-AmAc | 16117.87 | 16094.26-16140.52 | 0.011[a] | CON ≠ ADV (1.90-fold increased in ADV)<br>PRE ≠ ADV (2.07-fold increased in ADV)<br>MOD≠ ADV (2.11-fold increased in ADV) |
| 29 | CM10-AmAc | 16320.30 | 16296.87-16349.18 | 0.003[b] | CON ≠ ADV (2.36-fold increased in ADV)<br>PRE ≠ ADV (2.73-fold increased in ADV)<br>EAR ≠ ADV (1.97-fold increased in ADV)<br>MOD≠ ADV (2.99-fold increased in ADV) |
| 30 | Q10-NaAc | 21018.23 | 20980.22-21073.08 | 0.020[b] | CON ≠ ADV (1.30-fold decreased in ADV)<br>PRE ≠ ADV (1.20-fold decreased in ADV)<br>$(p < 0.14)$[c] |
| 31 | Q10-Tris | 37324.17 | 37166.16-37590.06 | 0.000[b] | CON ≠ ADV (1.33-fold decreased in ADV)<br>PRE ≠ ADV (1.56-fold decreased in ADV) |
| 31 | Q10-NaAc | 37415.98 | 36906.53-37633.64 | 0.037[b] | CON ≠ ADV (1.29-fold decreased in ADV)<br>PRE ≠ ADV (1.39-fold decreased in ADV)<br>EAR ≠ ADV (1.15-fold decreased in ADV)<br>$(p < 0.17)$[c] |
| 32 | Q10-Tris | 41829.80 | 41611.37-42059.30 | 0.004[a] | PRE ≠ ADV (1.53-fold decreased in ADV) |
| 33 | Q10-NaAc | 50472.78 | 50056.68-50933.57 | 0.018[b] | CON ≠ EAR (1.42-fold increased in EAR) |
| 34 | Q10-Tris | 56159.58 | 55976.01-56218.65 | 0.008[a] | PRE ≠ ADV (1.54-fold decreased in ADV) |

[a]Group means were found to be unequal by one-way ANOVA.
[b]Group means were found to be unequal by Welch's test.
[c]Group means were unequal by Welch's test but no individual groups were different at the 95% level by Tamhane's test.

The groups significant at the 80% level for Tamhane's test are reported.

In total, there were 32 peaks found to have statistically significant differences in the means of all groups in the three data sets. In the Q10-Tris data set, there were eight peaks showing statistically significant differences in the mean peak intensity of the groups as a whole. In the Q10-NaAc data set, there were 16 peaks displaying statistically significant differences in the mean peak intensity of the groups. In the CM10-AmAc data set, there were 12 peaks showing statistically significant differences in the mean peak intensity of the groups. Of these peaks differing between the groups, there was some overlap between the three data sets. Namely, peaks 8 and 31 both showed a statistically significant difference between the mean peak intensity of the groups in both the Q10-Tris and Q10-NaAc data sets. Some group comparisons in the Q10-NaAc data set found using Welch's test did not show any significant differences using Tamhane's T2 at the 95% level, presumably because of the conservative nature of this multiple comparison test. Where this was the case, groups differing at the 80% level were given as the groups most likely to cause the difference detected by Welch's test.

For each statistically significant group difference, a fold-change between the means of the groups was calculated and displayed in Table 9. There were a total of 59 individual group differences with mean peak intensity fold-changes of greater that 1.5 and these derived from 29 distinct peaks. These changes therefore likely represent the most robust and important differences between the groups.

Figure 8:
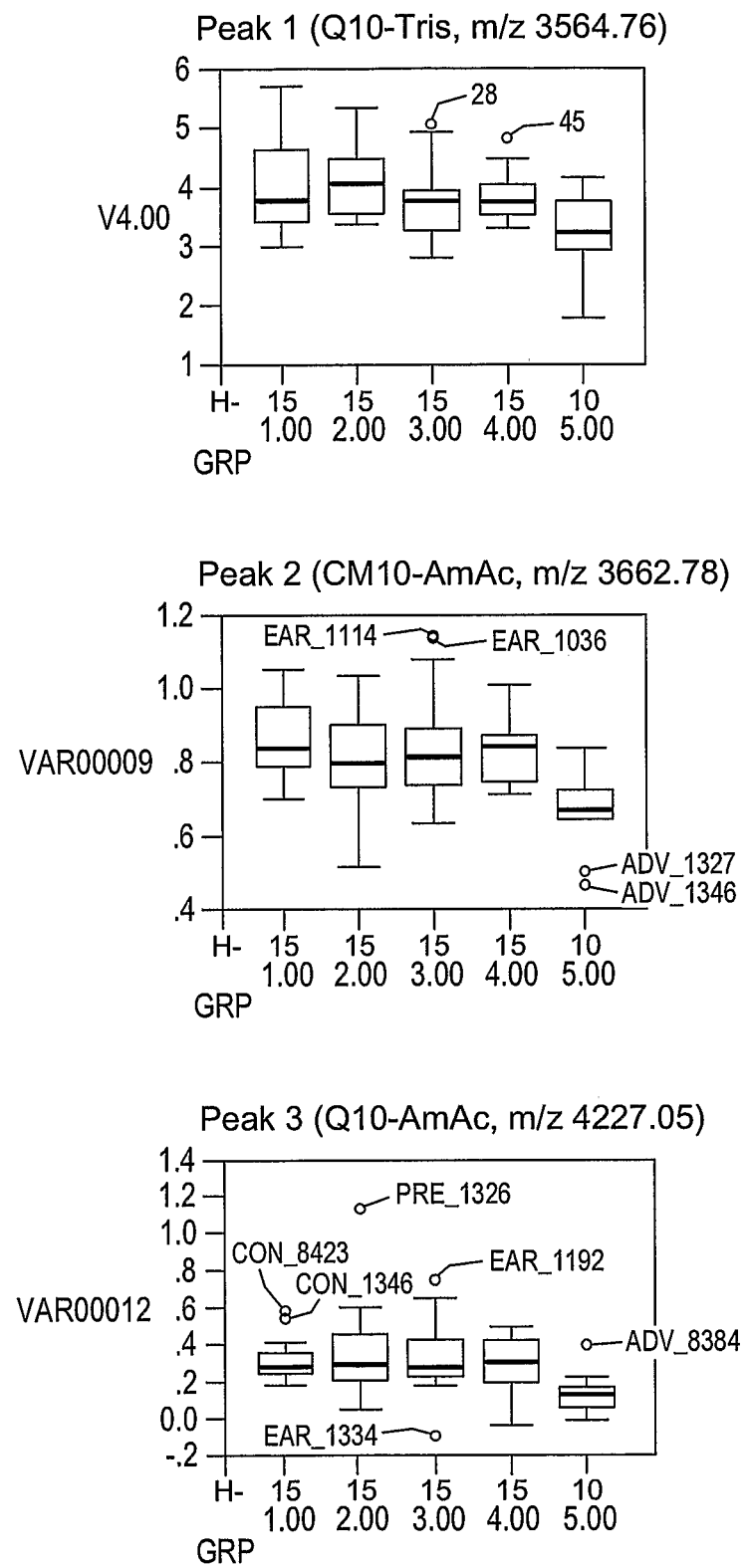
FIG. 8 shows box and whisker plots of significantly different peak intensities, as explained in Example 3.
Figure 8:
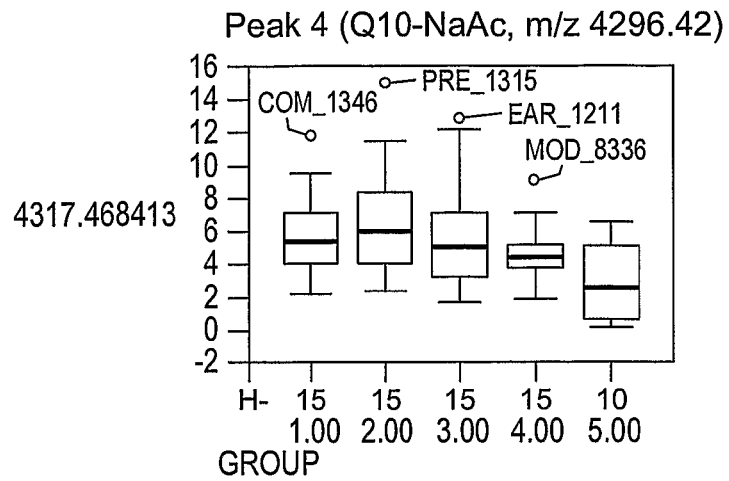
Figure 8:
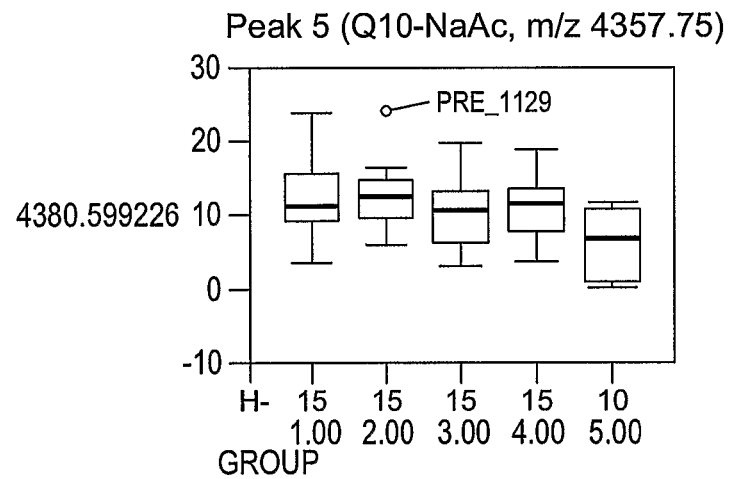
Figure 8:
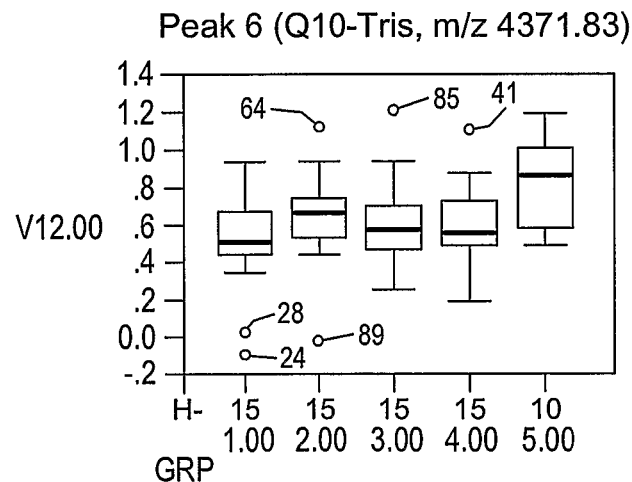
Figure 8:
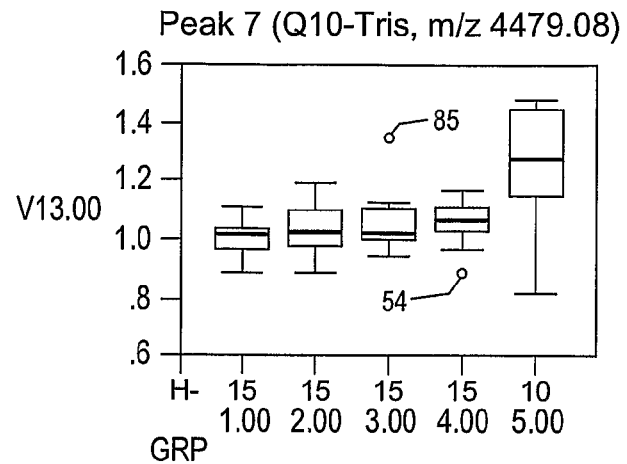
Figure 8:
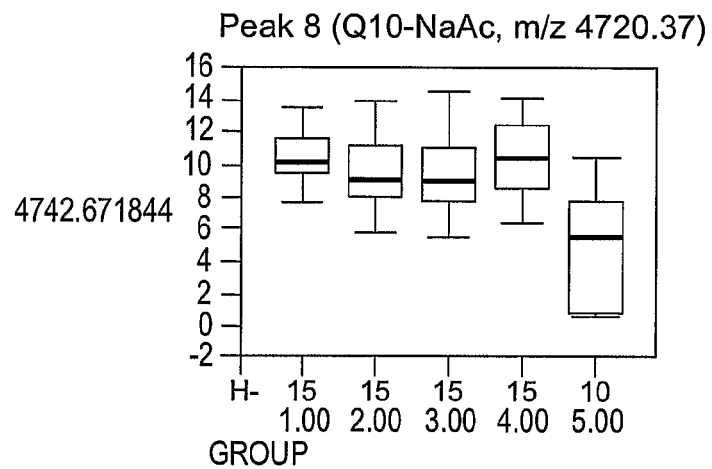
Figure 8:
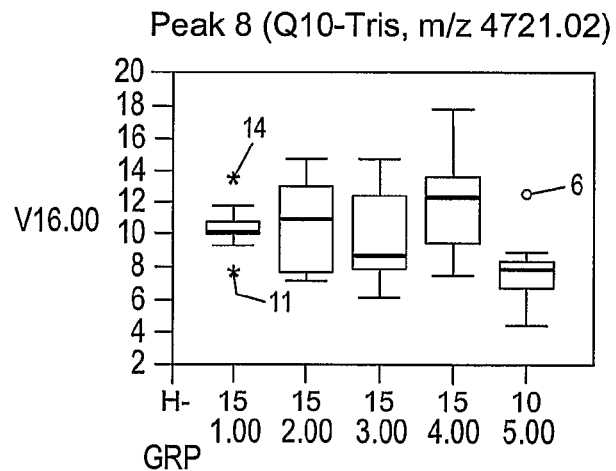
Figure 8:
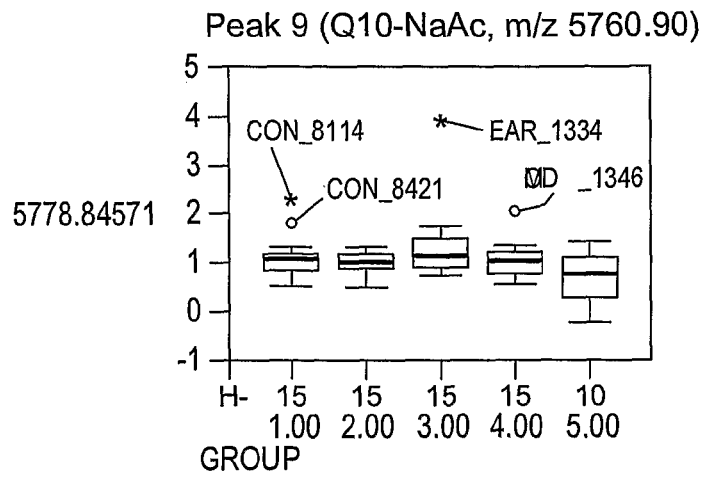
Figure 8:
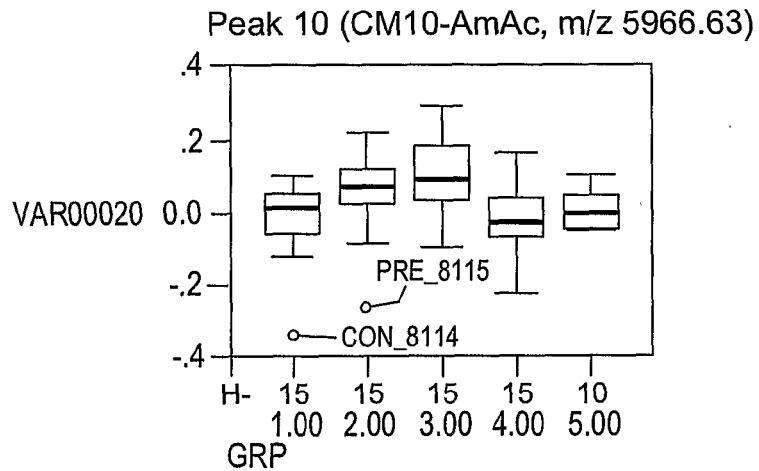
Figure 8:
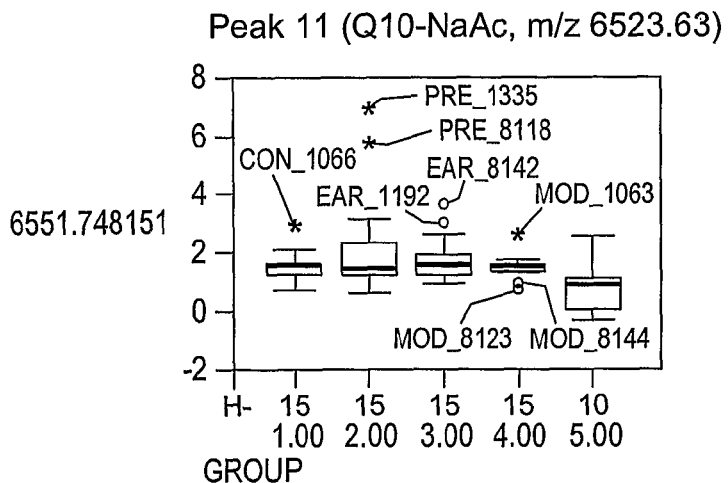
Figure 8:
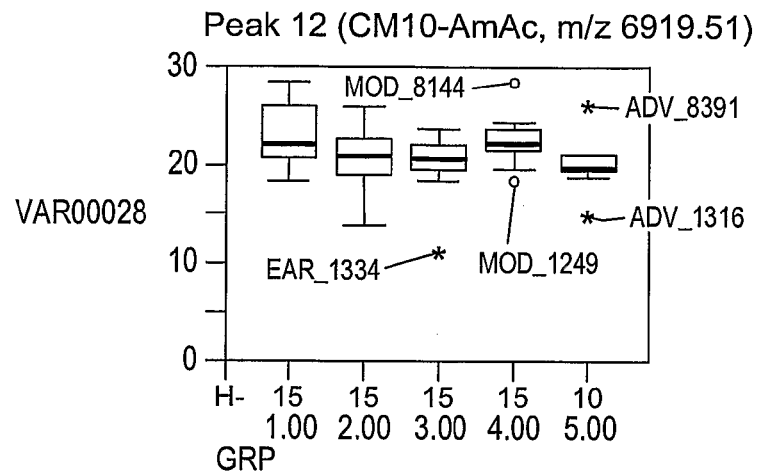
Figure 8:
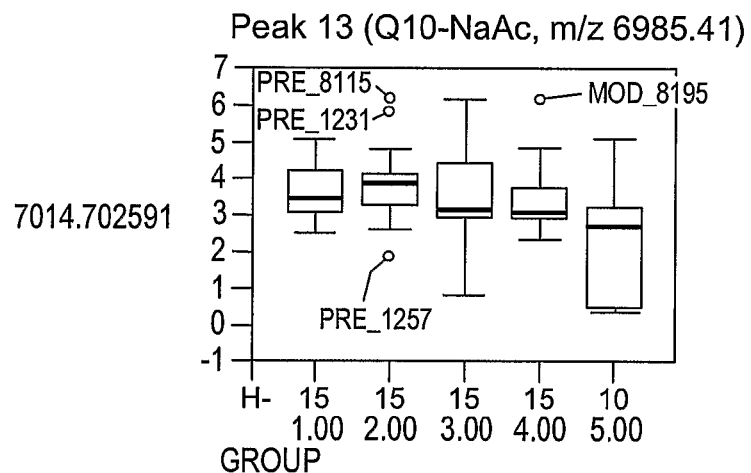
Figure 8:
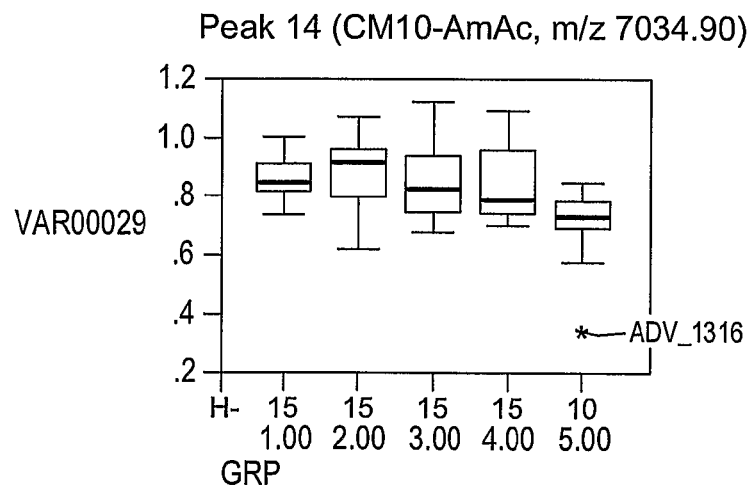
Figure 8:
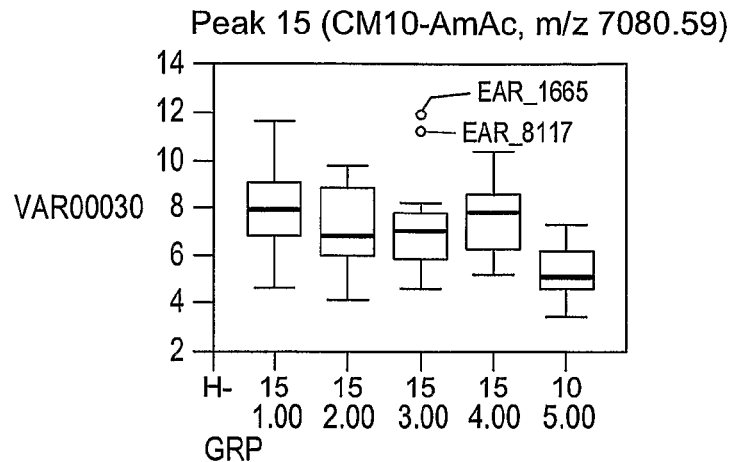
Figure 8:
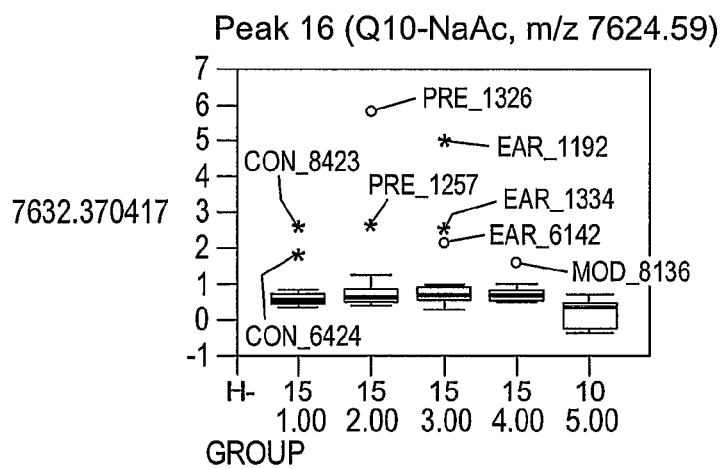
Figure 8:
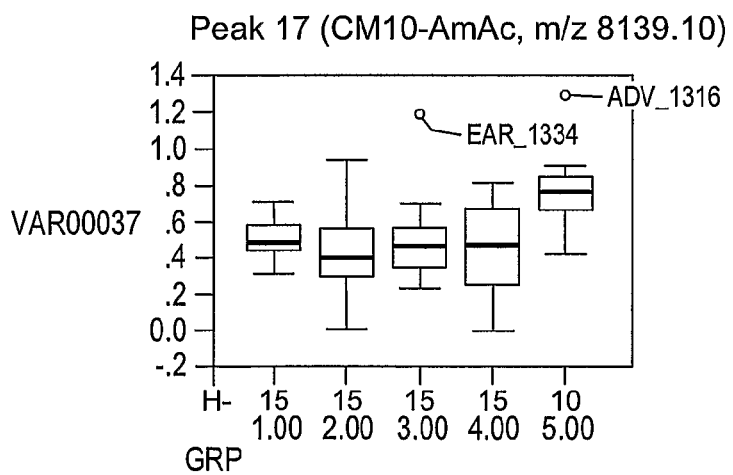
Figure 8:
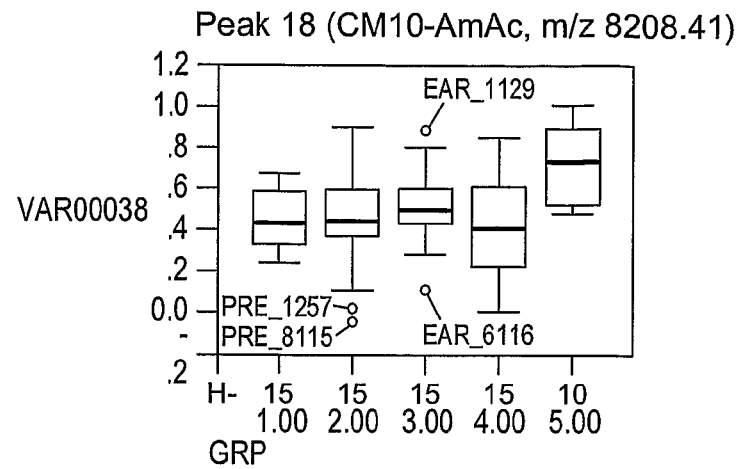
Figure 8:
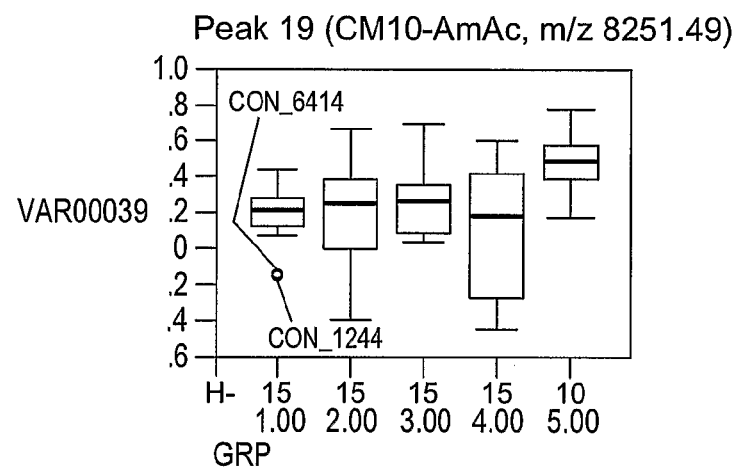
Figure 8:
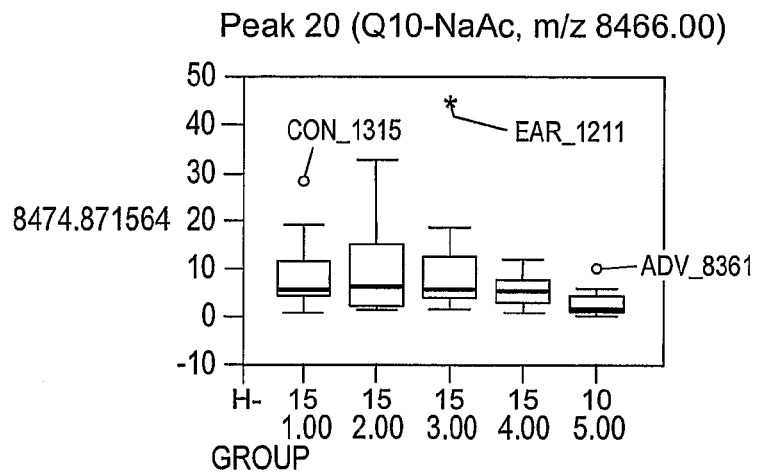
Figure 8:
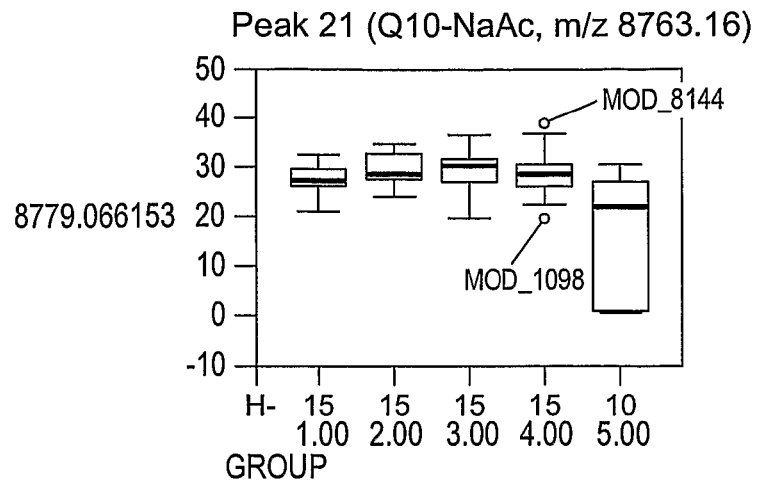
Figure 8:
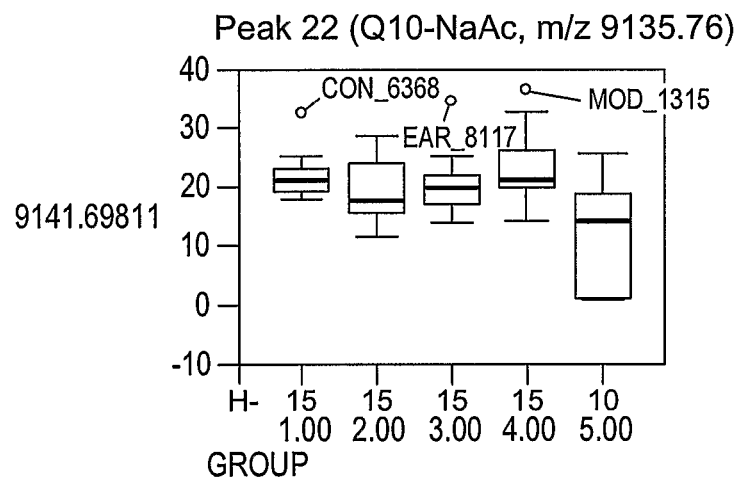
Figure 8:
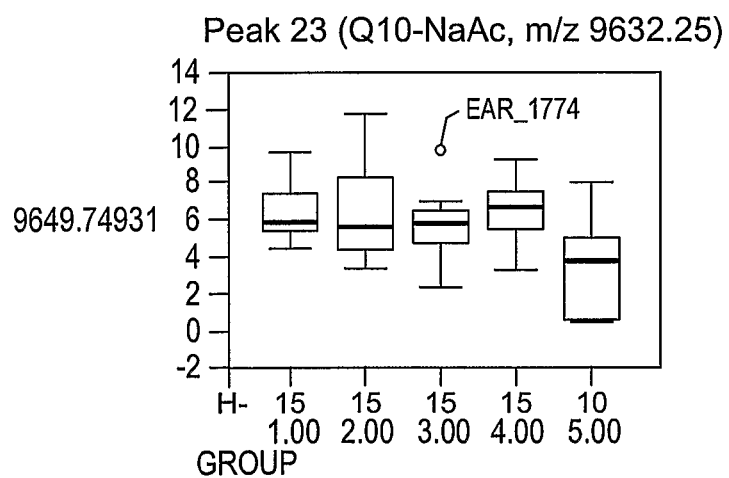
Figure 8:
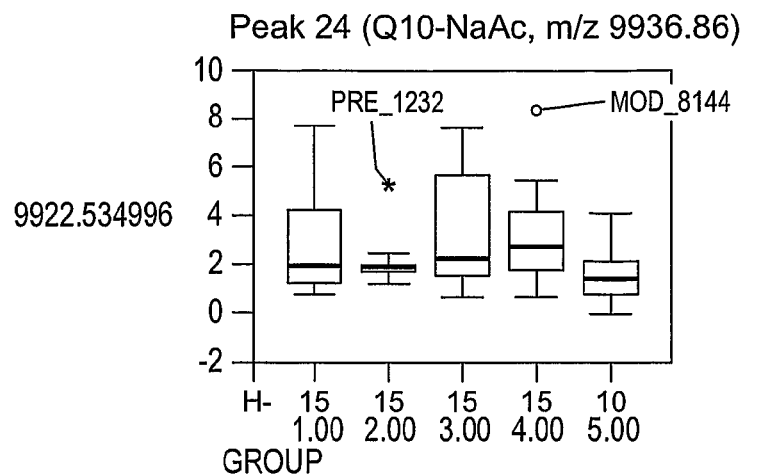
Figure 8:
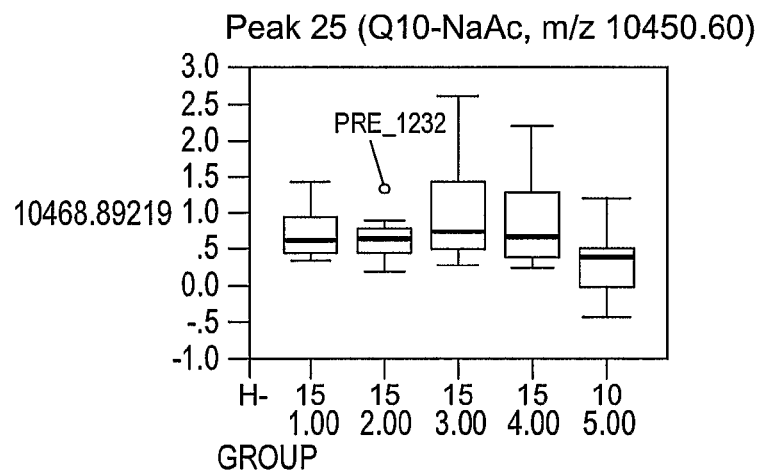
Figure 8:
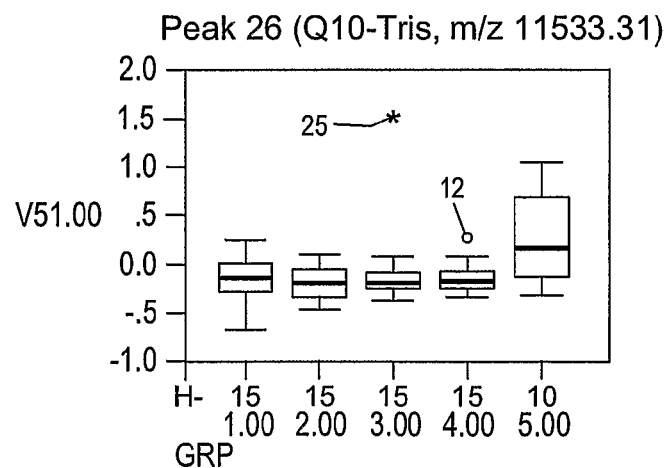
Figure 8:
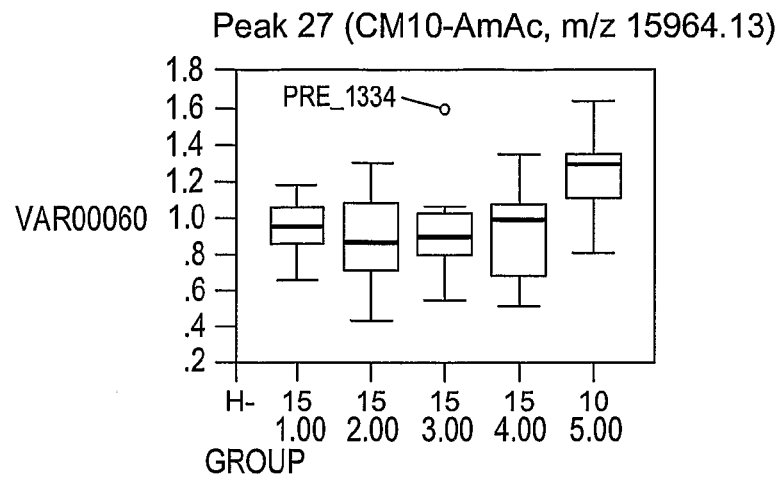
Figure 8:
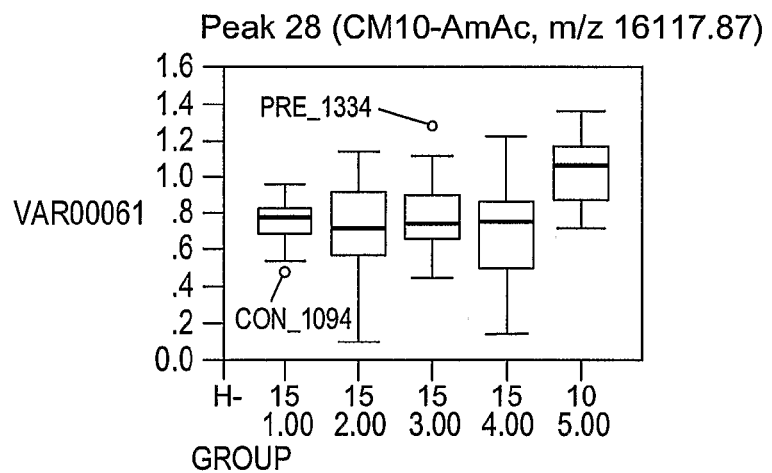
Figure 8:
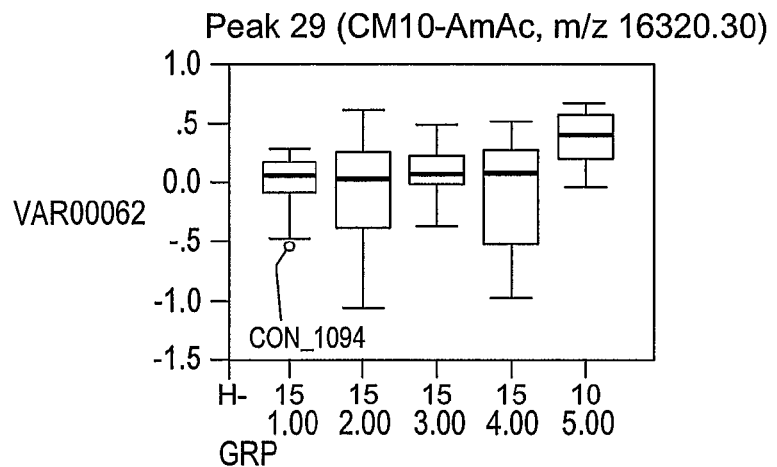
Figure 8:
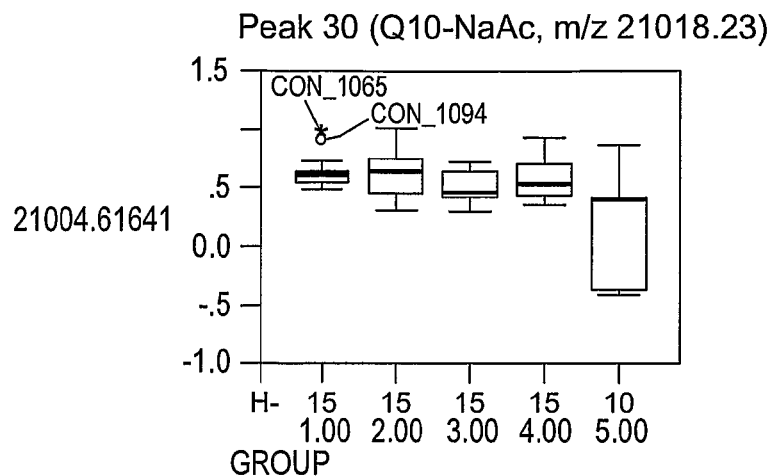
Figure 8:
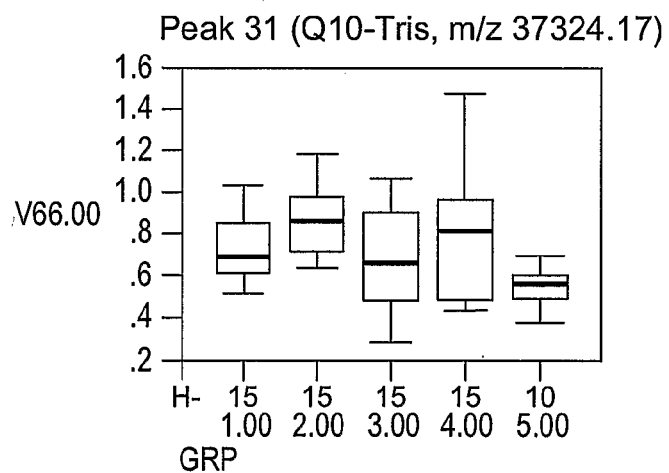
Figure 8:
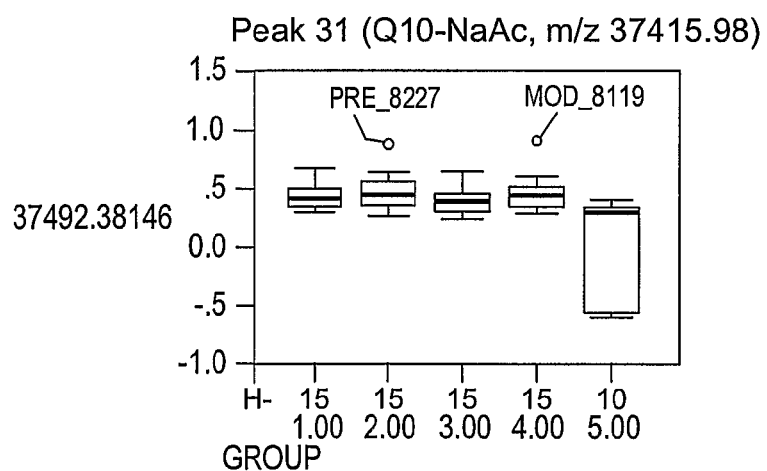
Figure 8:
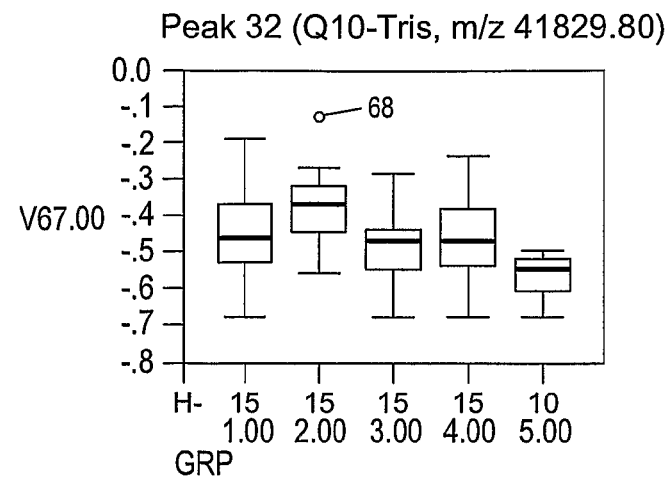
Figure 8:
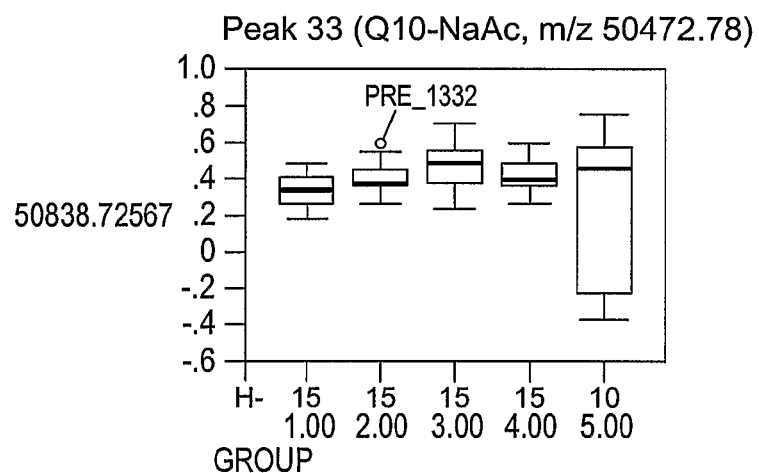
Figure 8:
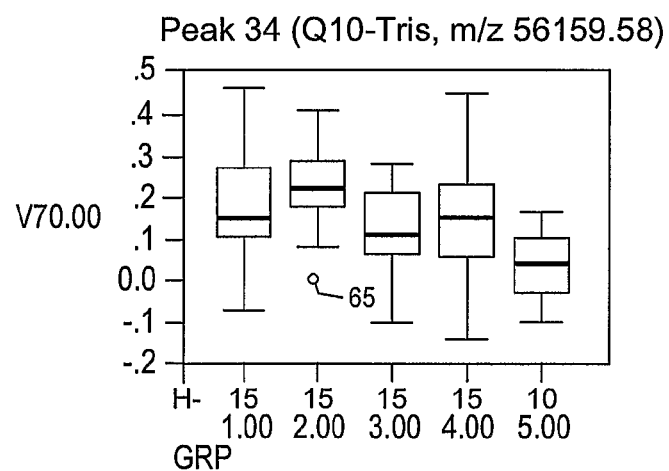

A prominent feature of the group differences listed in Table 9 is that the ADV group is the most often statistically different group compared to the other groups. There were a total of 82 individual group differences found and of these, 78 were a comparison of the ADV group with one of the other groups. This result does not necessarily imply that the changes observed only occurred in the advanced stages of HD, only that if the changes did progress with the disease that they were not large enough to be of statistical significance by the tests used. FIG. 8 shows box and whisker plots summarising the distributions of the peak intensities of the statistically differing peaks in each group. For each peak, the data set and m/z value are given along with a box and whisker plot showing the distribution of values within each group. The groups are labelled 1 (CON), 2 (PRE), 3 (EAR), 4 (MOD) and 5 (ADV).

SUMMARY

Figure 7:
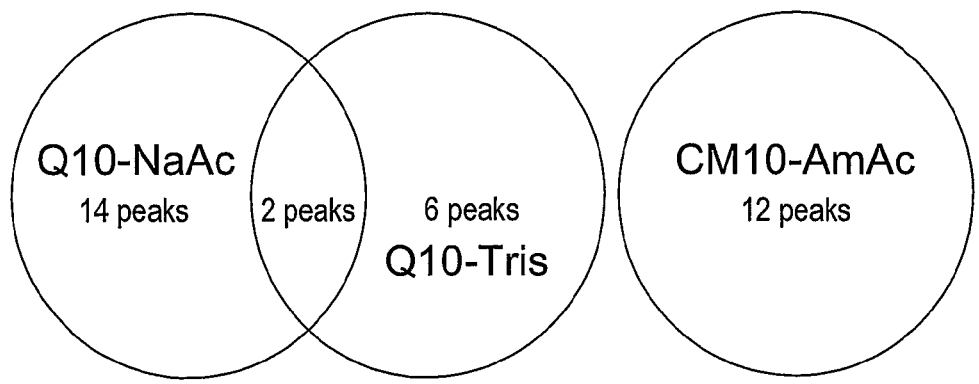
FIG. 7 is a Venn diagram displaying the number and overlap of statistically different peaks in three experimental data sets, as explained in Example 3.

The SELDI analysis of samples from the CON and HD groups detected in excess of 200 peaks in across three data sets. Of these peaks, 36 were found to be statistically different between one or more groups and two of these peaks were found to differ in both the Q10-Tris and Q10-NaAc data sets, giving 34 individually changing peaks. The number and overlap of the statistically different peaks in the three experimental data sets is displayed graphically in the form of a Venn diagram in FIG. 7. Of these 34 distinct peaks, 29 showed fold-changes between one or more groups of greater than 1.5-fold.

Further results are shown below in Table 10. This is a summary of all the proteins we have identified in material extracted from the SELDI chips. Any of the peaks we have observed in the SELDI profiles originate from any of the proteins listed in the table, either as the expected mature proteins or fragments of the proteins. This list of proteins and any fragments thereof thus constitute sequences that would feasibly generate the m/z values we see in the SELDI spectra.

TABLE 10

| Swiss Prot accession number | Protein name |
|---|---|
| P00738 | Haptoglobin precursor |
| P01009 | Alpha-1-antitrypsin precursor |
| P01024 | Complement C3 precursor |
| P01620 | Ig kappa chain V-III region |
| P01834 | Ig kappa chain C region |
| P01842 | Ig lambda chain C regions |
| P01857 | Ig gamma-1 chain C region |
| P01859 | Ig gamma-2 chain C region |
| P01876 | Ig alpha-1 chain C region |
| P02647 | Apolipoprotein A-I precursor |
| P02649 | Apolipoprotein E precursor |

TABLE 10-continued

| Swiss Prot accession number | Protein name |
|---|---|
| P02652 | Apolipoprotein A-II precursor |
| P02655 | Apolipoprotein C-II precursor |
| P02656 | Apolipoprotein C-III precursor |
| P02671 | Fibrinogen alpha/alpha-E chain precursor |
| P02763 | Alpha-1-acid glycoprotein 1 precursor |
| P02766 | Transthyretin precursor |
| P02768 | Serum albumin precursor |
| P02787 | Serotransferrin precursor |
| P04196 | Histidine-rich glycoprotein precursor |
| P06727 | Apolipoprotein A-IV precursor |
| P19652 | Alpha-1-acid glycoprotein 2 precursor |
| P68871/P02042 | Hemoglobin beta chain/Hemoglobin delta chain |
| P10909 | Clusterin |

We have correlated 6 of the 34 peak m/z observed in SELDI to the sequences indicated below. The following Table 11 refers to Master peak numbers indicated in Table 9 and correlates SELDI peak m/z with protein sequence information from LC/MS/MS results.

TABLE 11

| Master Peak No. | Peak m/z | Protein | Swiss Prot Accession No. | Amino acid Residues (as given in Swiss Prot database entry) |
|---|---|---|---|---|
| 13 | 6985.41 | Apolipoprotein A-II | P02652 | 39-100 |
| 16 | 7624.59 | Apolipoprotein A-II | P02652 | 34-100 |
| 18 | 8208.41 | Apolipoprotein C-II | P02655 | 29-101 |
| 19 | 8251.49 | Apolipoprotein A-II | P02652 | 28-100 |
| 20 | 8466.00 | Apolipoprotein C-II | P02655 | 27-101 |
| 21 | 8763.16 | Apolipoprotein C-III | P02656 | 21-99 (Expected Mature form) |

Each of the above-cited publications and database references is herein incorporated by reference to the extent to which it is relied on herein.

The invention claimed is:

1. A method for monitoring the progression of Huntington's Disease in a diagnostic sample of a valid body tissue taken from a living human subject having Huntington's Disease, which comprises
   detecting the concentration of Clusterin precursor (SwissProt Acc. No, P10909) in the diagnostic sample, and comparing it with the concentration of Clusterin precursor in an earlier sample from the same subject or with a standard value typical of a stage of the disease; and
   determining the progression of Huntington's disease in the human subject based on the comparison,
   wherein the progression of Huntington's Disease is monitored up to the moderate stage.

2. A method according to claim 1, which comprises detecting an increased concentration of Clusterin precursor in the diagnostic sample, compared with an earlier sample from the same subject.

3. A method according to claim 1 or 2, wherein the detection is performed on the diagnostic sample by a binding assay for the Clusterin precursor.

4. A method according to claim 3, wherein the binding assay comprises causing the Clusterin precursor of the diagnostic sample to interact with a specific binding partner and detecting the interaction.

5. A method according to claim 4, wherein the specific binding partner is a labelled antibody that recognizes the Clusterin precursor.

6. A method according to claim 5, wherein the antibody is immobilized on a solid phase.

7. A method according to claim 5, wherein the antibody is immobilized on beads or on a chip.

8. A method according to claim 1 or 2, wherein the diagnostic sample is subjected to two dimensional gel electrophoresis to yield a stained gel and an altered concentration of the Clusterin precursor is detected by an increased or decreased intensity of a protein-containing spot on the stained gel, compared with a corresponding control gel.

9. A method according to claim 1 or 2, wherein the valid body tissue is a body fluid.

10. A method according to claim 1 or 2, wherein the valid body tissue is of brain or nerve tissue.

11. A method according to claim 1 or 2, wherein a particular stage of Huntington's disease is diagnosed.

12. A method according to claim 11, wherein the progression of Huntington's disease in a subject is monitored by carrying out diagnoses on samples taken at intervals from the same subject.

13. A method according to claim 11, wherein an increased level of clusterin precursor compared to the previous level in an earlier sample from the same individual indicates an increase in severity of disease.

14. A method according to claim 11, wherein the progression of Huntington's disease in a subject is monitored by measuring the level of clusterin precursor (SwissProt Acc. No. P10909), and optionally an additional protein selected from the group consisting of apolipoprotein A-IV precursor (SwissProt Acc, No. P06727), beta actin (SwissProt Acc. No. P60709), and combinations thereof, whereby an increased level of one or more of these proteins compared to the respective previous level of the one or more proteins in an earlier sample from the same individual indicates an increase in severity of disease.

15. A method according to claim 11, wherein the monitoring of the progression of Huntington's disease is used to monitor the efficacy of treatment.

16. A method according to claim 1 or 2, wherein another disease, which may or may not be neurological, is diagnosed in the same sample of body tissue, by a method which comprises detecting an increased concentration of another protein in the diagnostic sample, compared with a sample of a control, normal human subject.

* * * * *